United States Patent
Alexander et al.

(10) Patent No.: US 11,633,194 B2
(45) Date of Patent: Apr. 25, 2023

(54) ADJUSTABLE IMPLANTABLE DEVICES AND ASSOCIATED METHODS

(71) Applicant: Shifamed Holdings, LLC, Campbell, CA (US)

(72) Inventors: Miles Alexander, Fremont, CA (US); Peter Andriola, Castro Valley, CA (US); Brian Fahey, Menlo Park, CA (US); William Jason Fox, San Mateo, CA (US); Anthony Pantages, San Jose, CA (US); Scott Robertson, Portland, OR (US); Jace Valls, San Jose, CA (US)

(73) Assignee: Shifamed Holdings, LLC, Campbell, CA (US)

(*) Notice: Subject to any disclaimer, the term of this patent is extended or adjusted under 35 U.S.C. 154(b) by 0 days.

(21) Appl. No.: 17/713,625

(22) Filed: Apr. 5, 2022

(65) Prior Publication Data

US 2022/0226000 A1    Jul. 21, 2022

Related U.S. Application Data

(63) Continuation of application No. 17/524,631, filed on Nov. 11, 2021.
(Continued)

(51) Int. Cl.
*A61B 17/12* (2006.01)
*A61B 17/11* (2006.01)
*A61M 27/00* (2006.01)

(52) U.S. Cl.
CPC ........ *A61B 17/12177* (2013.01); *A61B 17/11* (2013.01); *A61B 17/1204* (2013.01);
(Continued)

(58) Field of Classification Search
CPC .......... A61B 17/12177; A61B 17/1204; A61B 17/12109; A61B 17/122
See application file for complete search history.

(56) References Cited

U.S. PATENT DOCUMENTS

| 5,197,978 A | 3/1993 | Hess |
| 5,611,338 A | 3/1997 | Gallup |

(Continued)

FOREIGN PATENT DOCUMENTS

| AU | 2005211243 | 8/2005 |
| AU | 2010344182 | 8/2012 |

(Continued)

OTHER PUBLICATIONS

Definition of "shunt". Merriam-Webster Dictionary. 2009.*
(Continued)

*Primary Examiner* — Kelly J Bekker
*Assistant Examiner* — Mikail A Mannan
(74) *Attorney, Agent, or Firm* — Perkins Coie LLP

(57) ABSTRACT

The present technology includes systems and methods for invasively adjusting implantable devices for selectively controlling fluid flow between a first body region and a second body region of a patient. For example, in many of the embodiments described herein, a catheter can be used to mechanically and/or electrically engage an implanted medical device. Once the catheter engages the medical device, the catheter can (i) increase a dimension associated with the medical device, such as through mechanical expansion forces, and/or (ii) decrease a dimension associated with the medical device, such as by heating a shape memory component of the medical device above a phase transition temperature.

19 Claims, 22 Drawing Sheets

Related U.S. Application Data

(60) Provisional application No. 63/164,481, filed on Mar. 22, 2021, provisional application No. 63/112,787, filed on Nov. 12, 2020.

(52) U.S. Cl.
CPC ..... *A61B 17/12109* (2013.01); *A61M 27/002* (2013.01); *A61M 2205/04* (2013.01); *A61M 2205/3331* (2013.01)

(56) References Cited

U.S. PATENT DOCUMENTS

| | | | |
|---|---|---|---|
| 6,077,298 A * | 6/2000 | Tu | A61F 2/82 623/1.19 |
| 6,120,534 A | 9/2000 | Ruiz | |
| 6,165,209 A | 12/2000 | Patterson et al. | |
| 6,240,322 B1 | 5/2001 | Peterfeso et al. | |
| 6,783,499 B2 | 8/2004 | Schwartz | |
| 6,909,920 B2 | 6/2005 | Lokhoff et al. | |
| 7,524,329 B2 | 4/2009 | Rucker | |
| 7,617,001 B2 | 11/2009 | Penner et al. | |
| 7,634,318 B2 | 12/2009 | Tran et al. | |
| 7,658,747 B2 | 2/2010 | Forde et al. | |
| 7,860,579 B2 | 12/2010 | Goetzinger et al. | |
| 8,043,360 B2 | 10/2011 | McNamara et al. | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,235,933 B2 | 8/2012 | Keren et al. | |
| 8,252,042 B2 | 8/2012 | McNamara et al. | |
| 8,328,751 B2 | 12/2012 | Keren et al. | |
| 8,460,372 B2 | 6/2013 | McNamara et al. | |
| 8,696,611 B2 | 4/2014 | Nitzan et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,882,697 B2 | 11/2014 | Celermajer et al. | |
| 8,951,223 B2 | 2/2015 | McNamara et al. | |
| 9,005,155 B2 | 4/2015 | Sugimoto | |
| 9,034,034 B2 | 5/2015 | Nitzan et al. | |
| 9,204,842 B2 | 12/2015 | Mothilal et al. | |
| 9,205,236 B2 | 12/2015 | McNamara et al. | |
| 9,232,997 B2 | 1/2016 | Sugimoto et al. | |
| 9,277,995 B2 | 3/2016 | Celermajer et al. | |
| 9,358,371 B2 | 6/2016 | McNamara et al. | |
| 9,456,812 B2 | 10/2016 | Finch et al. | |
| 9,610,041 B2 | 4/2017 | Foster et al. | |
| 9,629,715 B2 | 4/2017 | Nitzan et al. | |
| 9,642,993 B2 | 5/2017 | McNamara et al. | |
| 9,649,480 B2 | 5/2017 | Sugimoto et al. | |
| 9,681,948 B2 | 6/2017 | Levi et al. | |
| 9,707,382 B2 | 7/2017 | Nitzan et al. | |
| 9,713,696 B2 | 7/2017 | Yacoby et al. | |
| 9,724,499 B2 | 8/2017 | Rottenberg et al. | |
| 9,757,107 B2 | 9/2017 | McNamara et al. | |
| 9,775,636 B2 | 10/2017 | Fazio et al. | |
| 9,918,856 B2 | 3/2018 | Favier et al. | |
| 9,937,036 B2 | 4/2018 | Sugimoto et al. | |
| 9,943,670 B2 | 4/2018 | Keren et al. | |
| 9,980,815 B2 | 5/2018 | Nitzan et al. | |
| 10,045,766 B2 | 8/2018 | McNamara et al. | |
| 10,076,403 B1 | 9/2018 | Eigler et al. | |
| 10,188,375 B2 | 1/2019 | McNamara et al. | |
| 10,207,087 B2 | 2/2019 | Keren | |
| 10,251,740 B2 | 4/2019 | Eigler et al. | |
| 10,292,690 B2 | 5/2019 | Celermajer et al. | |
| 10,350,384 B2 | 7/2019 | Farnan et al. | |
| 10,357,357 B2 | 7/2019 | Levi et al. | |
| 10,368,981 B2 | 8/2019 | Nitzan et al. | |
| 10,376,680 B2 | 8/2019 | McNamara et al. | |
| 10,398,421 B2 | 9/2019 | Celermajer | |
| 10,405,903 B1 | 9/2019 | Biesinger et al. | |
| 10,413,284 B2 | 9/2019 | McNamara et al. | |
| 10,413,286 B2 | 9/2019 | McNamara et al. | |
| 10,463,477 B2 | 11/2019 | Forcucci et al. | |
| 10,463,490 B2 | 11/2019 | Rottenberg et al. | |
| 10,471,251 B1 | 11/2019 | Manicka | |
| 10,478,594 B2 | 11/2019 | Yacoby et al. | |
| 10,568,751 B2 | 2/2020 | McNamara | |
| 10,588,611 B2 | 3/2020 | Magnin et al. | |
| 10,610,210 B2 | 4/2020 | Finch et al. | |
| 10,624,621 B2 | 4/2020 | Celermajer | |
| 10,632,292 B2 | 4/2020 | Forcucci et al. | |
| 10,639,459 B2 | 5/2020 | Nitzan et al. | |
| 10,667,896 B2 | 6/2020 | Delaney, Jr. et al. | |
| 10,675,450 B2 | 6/2020 | Finch | |
| 10,828,151 B2 | 11/2020 | Nitzan et al. | |
| 10,835,394 B2 | 11/2020 | Nae et al. | |
| 10,898,698 B1 | 1/2021 | Eigler et al. | |
| 10,912,645 B2 | 2/2021 | Rottenberg et al. | |
| 10,925,706 B2 | 2/2021 | Eigler et al. | |
| 10,932,786 B2 | 3/2021 | McNamara et al. | |
| 10,940,296 B2 | 3/2021 | Keren | |
| 10,945,716 B2 | 3/2021 | Chen et al. | |
| 11,135,410 B2 | 10/2021 | Finch et al. | |
| 11,253,685 B2 | 2/2022 | Fahey et al. | |
| 2002/0072656 A1 | 6/2002 | Vantassel et al. | |
| 2002/0161427 A1 | 10/2002 | Rabkin et al. | |
| 2002/0177891 A1 | 11/2002 | Miles et al. | |
| 2003/0127090 A1 | 7/2003 | Gifford et al. | |
| 2003/0163190 A1 * | 8/2003 | LaFont | A61F 2/958 600/101 |
| 2004/0158143 A1 | 8/2004 | Flaherty et al. | |
| 2004/0186566 A1 | 9/2004 | Hindrichs et al. | |
| 2005/0004641 A1 | 1/2005 | Pappu | |
| 2005/0060030 A1 | 3/2005 | Lashinski et al. | |
| 2005/0101946 A1 | 5/2005 | Govari et al. | |
| 2005/0148925 A1 | 7/2005 | Rottenberg et al. | |
| 2005/0159789 A1 | 7/2005 | Brockway et al. | |
| 2005/0204811 A1 | 9/2005 | Neff | |
| 2005/0288722 A1 | 12/2005 | Eigler et al. | |
| 2006/0009810 A1 | 1/2006 | Mann et al. | |
| 2006/0047205 A1 | 3/2006 | Ludomirsky et al. | |
| 2006/0064135 A1 | 3/2006 | Brockway | |
| 2006/0116625 A1 | 6/2006 | Renati et al. | |
| 2006/0200030 A1 | 9/2006 | White et al. | |
| 2007/0010837 A1 | 1/2007 | Tanaka | |
| 2007/0088220 A1 | 4/2007 | Stahmann | |
| 2007/0088223 A1 | 4/2007 | Mann et al. | |
| 2007/0118039 A1 | 5/2007 | Bodecker et al. | |
| 2007/0150019 A1 | 6/2007 | Youker et al. | |
| 2007/0282157 A1 | 12/2007 | Rottenberg et al. | |
| 2008/0033527 A1 | 2/2008 | Nunez et al. | |
| 2008/0097276 A1 | 4/2008 | Bertrand et al. | |
| 2008/0108904 A1 | 5/2008 | Heil | |
| 2008/0119891 A1 | 5/2008 | Miles et al. | |
| 2008/0127689 A1 | 6/2008 | McCusker et al. | |
| 2008/0171941 A1 | 7/2008 | Huelskamp et al. | |
| 2008/0208083 A1 | 8/2008 | Lin et al. | |
| 2009/0025459 A1 | 1/2009 | Zhang et al. | |
| 2009/0036975 A1 | 2/2009 | Ward et al. | |
| 2009/0243956 A1 | 10/2009 | Keilman et al. | |
| 2009/0270742 A1 | 10/2009 | Wolinsky et al. | |
| 2009/0281597 A1 | 11/2009 | Parramon et al. | |
| 2010/0063375 A1 | 3/2010 | Kassab et al. | |
| 2010/0076366 A1 | 3/2010 | Henderson, Sr. et al. | |
| 2010/0076517 A1 | 3/2010 | Imran | |
| 2010/0106028 A1 | 4/2010 | Penner et al. | |
| 2010/0168672 A1 | 7/2010 | Carr | |
| 2010/0179449 A1 | 7/2010 | Chow et al. | |
| 2010/0241241 A1 | 9/2010 | McKnight et al. | |
| 2010/0249560 A1 | 9/2010 | Levinson et al. | |
| 2010/0262021 A1 | 10/2010 | Yadav et al. | |
| 2010/0262036 A1 | 10/2010 | Najafi et al. | |
| 2010/0275592 A1 | 11/2010 | Topliss et al. | |
| 2010/0298930 A1 | 11/2010 | Orlov | |
| 2011/0082377 A1 | 4/2011 | Ah | |
| 2011/0218480 A1 | 9/2011 | Rottenberg et al. | |
| 2011/0218481 A1 | 9/2011 | Rottenberg et al. | |
| 2011/0257723 A1 | 10/2011 | McNamara | |
| 2011/0264194 A1 | 10/2011 | Griswold | |
| 2011/0282217 A1 | 11/2011 | Nashet | |

(56) References Cited

U.S. PATENT DOCUMENTS

| | | |
|---|---|---|
| 2011/0295183 A1 | 12/2011 | Finch et al. |
| 2012/0059431 A1 | 3/2012 | Williams et al. |
| 2012/0229272 A1 | 9/2012 | Jacob et al. |
| 2012/0265296 A1 | 10/2012 | McNamara et al. |
| 2012/0283773 A1 | 11/2012 | Van Tassel et al. |
| 2012/0290062 A1 | 11/2012 | McNamara et al. |
| 2013/0085350 A1 | 4/2013 | Schugt et al. |
| 2013/0123569 A1 | 5/2013 | Gross |
| 2013/0144379 A1 | 6/2013 | Najafi et al. |
| 2013/0178783 A1 | 7/2013 | McNamara et al. |
| 2013/0178784 A1 | 7/2013 | McNamara et al. |
| 2013/0190799 A1 | 7/2013 | Clark |
| 2013/0192611 A1 | 8/2013 | Taepke, II et al. |
| 2013/0197423 A1 | 8/2013 | Keren et al. |
| 2013/0211221 A1 | 8/2013 | Sunnarborg et al. |
| 2013/0253343 A1 | 9/2013 | Waldhauser et al. |
| 2013/0293025 A1 | 11/2013 | Xu et al. |
| 2014/0012342 A1 | 1/2014 | Penner et al. |
| 2014/0046427 A1 | 2/2014 | Michalak |
| 2014/0128795 A1 | 5/2014 | Karen et al. |
| 2014/0128796 A1 | 5/2014 | Keren et al. |
| 2014/0135647 A1 | 5/2014 | Wolf, II |
| 2014/0163449 A1 | 6/2014 | Rottenberg et al. |
| 2014/0213915 A1 | 7/2014 | Doan et al. |
| 2014/0213959 A1 | 7/2014 | Nitzan et al. |
| 2014/0222040 A1 | 8/2014 | Park et al. |
| 2014/0277054 A1 | 9/2014 | McNamara et al. |
| 2014/0306807 A1 | 10/2014 | Rowland et al. |
| 2015/0034217 A1 | 2/2015 | Vad |
| 2015/0084585 A1 | 3/2015 | Moran |
| 2015/0119796 A1 | 4/2015 | Finch |
| 2015/0148731 A1 | 5/2015 | McNamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph et al. |
| 2015/0230843 A1 | 8/2015 | Palmer et al. |
| 2015/0287544 A1 | 10/2015 | Irazoqui et al. |
| 2016/0022423 A1 | 1/2016 | McNamara et al. |
| 2016/0089079 A1 | 3/2016 | Stein |
| 2016/0151179 A1 | 6/2016 | Favier et al. |
| 2016/0158561 A1 | 6/2016 | Reddy |
| 2016/0235999 A1 | 8/2016 | Nuta et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0168463 A1 | 6/2018 | Morris et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0310839 A1 | 11/2018 | McCaffrey et al. |
| 2019/0000327 A1 | 1/2019 | Doan |
| 2019/0014993 A1 | 1/2019 | Kaiser |
| 2019/0015103 A1 | 1/2019 | Sharma |
| 2019/0021861 A1 | 1/2019 | Finch |
| 2019/0150758 A1 | 5/2019 | Sailey et al. |
| 2019/0167197 A1 | 6/2019 | Abuuassar et al. |
| 2019/0173505 A1 | 6/2019 | Koyama |
| 2019/0175883 A1 | 6/2019 | Wessler et al. |
| 2019/0192864 A1 | 6/2019 | Koop et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0298556 A1 | 10/2019 | Bohn et al. |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2019/0350519 A1 | 11/2019 | Bailey et al. |
| 2020/0008870 A1 | 1/2020 | Gruba et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0188143 A1 | 6/2020 | McNamara |
| 2020/0196876 A1 | 6/2020 | Minor et al. |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0253615 A1 | 8/2020 | Melanson et al. |
| 2020/0260991 A1 | 8/2020 | Rowland et al. |
| 2020/0261705 A1 | 8/2020 | Nitzan et al. |
| 2020/0268515 A1 | 8/2020 | Vettukattil et al. |
| 2020/0315599 A1 | 10/2020 | Nae et al. |
| 2020/0368505 A1 | 11/2020 | Nae et al. |
| 2021/0030273 A1 | 2/2021 | Huang et al. |
| 2021/0038230 A1 | 2/2021 | Larsen et al. |
| 2021/0052378 A1 | 2/2021 | Nitzan et al. |
| 2021/0059527 A1 | 3/2021 | Najafi |
| 2021/0085935 A1 | 3/2021 | Fahey et al. |
| 2021/0100513 A1 | 4/2021 | Sahmanyar et al. |
| 2021/0100665 A1 | 4/2021 | Nae et al. |
| 2021/0121179 A1 | 4/2021 | Ben-David et al. |
| 2021/0145331 A1 | 5/2021 | Simpson et al. |
| 2021/0153776 A1 | 5/2021 | Minar et al. |
| 2021/0177508 A1 | 6/2021 | Kellerman |
| 2021/0205590 A1 | 7/2021 | Fahey et al. |
| 2021/0212638 A1 | 7/2021 | Golda et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0298763 A1 | 9/2021 | Stahmann et al. |
| 2021/0299425 A1 | 9/2021 | Kume et al. |
| 2021/0299430 A1 | 9/2021 | Ratz et al. |
| 2021/0361238 A1 | 11/2021 | Bak-Boychuk et al. |
| 2021/0361257 A1 | 11/2021 | Eimer et al. |
| 2021/0370032 A1 | 12/2021 | Fahey et al. |
| 2021/0401418 A1 | 12/2021 | Dang et al. |
| 2022/0039670 A1 | 2/2022 | Berrada et al. |
| 2022/0039671 A1 | 2/2022 | Fahey |
| 2022/0117555 A1 | 4/2022 | Zarbatany et al. |
| 2022/0118228 A1 | 4/2022 | Fahey et al. |
| 2022/0151618 A1 | 5/2022 | Eigler et al. |
| 2022/0167861 A1 | 6/2022 | Stahmann |
| 2022/0184355 A1 | 6/2022 | Fahey et al. |
| 2022/0192677 A1 | 6/2022 | Wedul et al. |
| 2022/0218355 A1 | 7/2022 | Wedul et al. |
| 2022/0218964 A1 | 7/2022 | Fahey et al. |
| 2022/0226623 A1 | 7/2022 | Fahey et al. |
| 2022/0240856 A1 | 8/2022 | Stahmann et al. |
| 2022/0265280 A1 | 8/2022 | Chamorro et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 A | 4/2019 |
| CN | 110536657 | 12/2019 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |

(56) References Cited

FOREIGN PATENT DOCUMENTS

| | | |
|---|---|---|
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |
| WO | WO2005074367 | 8/2005 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2018024868 | 2/2018 |
| WO | WO2018132549 | 7/2018 |
| WO | WO2018158747 | 9/2018 |
| WO | WO2019186101 | 2/2019 |
| WO | WO2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021126699 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021224736 | 11/2021 |
| WO | WO2022046921 | 3/2022 |
| WO | WO2022076601 | 4/2022 |
| WO | WO2022081980 | 4/2022 |
| WO | WO2022103973 | 5/2022 |
| WO | WO2022192280 | 9/2022 |
| WO | WO2022266465 | 12/2022 |

OTHER PUBLICATIONS

Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
International Search Report and Written Opinion received for International Application No. PCT/US19/69106 filed Dec. 31, 2019; Applicant: Shifamed Holdings, LLC; dated Mar. 23, 2020; 10 pages.
International Search Report and Written Opinion received for International Application No. PCT/US20/49996 filed Sep. 9, 2020; Applicant: Shifamed Holdings, LLC; dated Feb. 17, 2021; 16 pages.
International Search Report and Written Opinion received for International Application No. PCT/US20/063360 filed Dec. 4, 2020; Applicant: Shifamed Holdings, LLC; dated Apr. 5, 2021; 13 pages.
International Search Report and Written Opinion received for International Application No. PCT/US20/64529 filed Dec. 11, 2020; Applicant: Shifamed Holdings, LLC; dated Apr. 8, 2021; 12 pages.
International Search Report and Written Opinion received for International Application No. PCT/US19/68354, filed Dec. 23, 2019; Applicant: Shifamed Holdings, LLC; dated Mar. 17, 2020; 11 pages.
International Search Report and Written Opinion received for International Application No. PCT/US21/16932, filed Feb. 5, 2021; Applicant: Shifamed Holdings, LLC; dated Jun. 3, 2021; 11 pages.
International Search Report and Written Opinion received for International Application No. PCT/US21/14433, filed Jan. 21, 2021; Applicant: Shifamed Holdings, LLC; dated May 14, 2021; 16 pages.
International Search Report and Written Opinion received for International Application No. PCT/US21/28926, filed Apr. 23, 2021; Applicant: Shifamed Holdings, LLC; dated Jul. 22, 2021; 16 pages.

(56) References Cited

OTHER PUBLICATIONS

International Search Report and Written Opinion received for International Application No. PCT/US20/12059, filed Jan. 2, 2020; Applicant: Shifamed Holdings, LLC; dated Jun. 5, 2020; 12 pages.

International Search Report and Written Opinion received for International Application No. PCT/US20/25509, filed Mar. 27, 2020; Applicant: Shifamed Holdings, LLC; dated Jun. 25, 2020; 9 pages.

International Search Report and Written Opinion received for International Application No. PCT/US20/26738, filed Apr. 3, 2020; Applicant: Shifamed Holdings, LLC; dated Jun. 30, 2020; 8 pages.

International Search Report and Written Opinion received for International Application No. PCT/US21/28931, filed Apr. 23, 2021; Applicant: Shifamed Holdings, LLC; dated Sep. 24, 2021; 20 pages.

International Search Report and Written Opinion received for International Application No. PCT/US21/27747, filed Apr. 16, 2021; Applicant: Shifamed Holdings, LLC; dated Oct. 1, 2021; 16 pages.

International Search Report and Written Opinion received for International Application No. PCT/US21/53836, filed Oct. 6, 2021; Applicant: Shifamed Holdings, LLC; dated Jan. 25, 2022; 20 pages.

International Search Report and Written Opinion received for International Application No. PCT/US21/47573, filed Aug. 25, 2021; Applicant: Shifamed Holdings, LLC; dated Feb. 3, 2022; 15 pages.

Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, pp. 9, col. 1, ln 5-6.

Hossain, M. et al. "In situ preparation of graphene-ZnO composites for enhanced graphite exfoliation and graphene-nylon-6 composite films," Journal of Applied Polymer Science, Dec. 5, 2016, vol. 134, No. 27, p. 8, ln 15-16.

International Search Report and Written Opinion received for International Application No. PCT/US21/58996, filed Nov. 11, 2021; Applicant: Shifamed Holdings, LLC; dated Feb. 7, 2022; 23 pages.

International Search Report and Written Opinion received for International Application No. PCT/US21/55191, filed Oct. 15, 2021; Applicant: Shifamed Holdings, LLC; dated Mar. 1, 2022; 12 pages.

Anomet Products "Conductive Nitinol Wire" Aug. 15, 2020, Retrieved from website <URL: https://helpx.adobe.com/acrobat/using/allow-or-block-links-internet.html?mv=product&mv2=acrobat>, 4 pages.

International Search Report and Written Opinion received for International Application No. PCT/US22/19374, filed Jun. 30, 2022; Applicant: Shifamed Holdings, LLC; dated Sep. 19, 2022; 10 pages.

International Search Report and Written Opinion received for International Application No. PCT/US22/35764, filed Jun. 30, 2022; Applicant: Shifamed Holdings, LLC; dated Sep. 19, 2022; 10 pages.

International Search Report and Written Opinion received for International Application No. PCT/US22/34027, filed Jun. 17, 2022; Applicant: Shifamed Holdings, LLC; dated Oct. 25, 2022; 8 pages.

International Search Report and Written Opinion received for International Application No. PCT/US22/34995, filed Jun. 24, 2022; Applicant: Shifamed Holdings, LLC; dated Nov. 18, 2022; 17 pages.

Perk et al., "Catheter-based left atrial appendage occlusion procedure: role of echocardiography," published on behalf of the European Society of Cardiology, Sep. 8, 2011, 7 pages.

Collado et al., "Left Atrial Appendage Occlusion for Stroke Prevention in Nonvalvular Atrial Fibrillation," Journal of the American Heart Association, Jun. 2021, 18 pages.

\* cited by examiner

200

201
Interfacing an energy delivery device with an implanted medical device

202
Using an energy delivery system on the energy delivery device to adjust a geometry of an actuator complex on the implanted device from a first geometry to a second geometry in a manner that is reversible 203
Decoupling the energy delivery device from the implanted medical device in a manner such that actuator complex remains in a geometry that is altered from the first geometry, and removing the delivery device from the body

301
Interfacing an energy delivery device with an implanted medical device that includes an actuator complex having an initial geometry 302
Using an energy delivery system on the energy delivery device to adjust a dimension of the actuator complex on the implanted device in a first direction 303
Using the energy delivery device to make a second adjustment of a dimension of the actuator complex on the implanted device in a second, opposite direction 304
Decoupling the energy delivery device from the implanted medical device in a manner such that actuator complex remains in a geometry that is altered form the initial geometry, and removing the delivery device from the body

*FIG. 3*

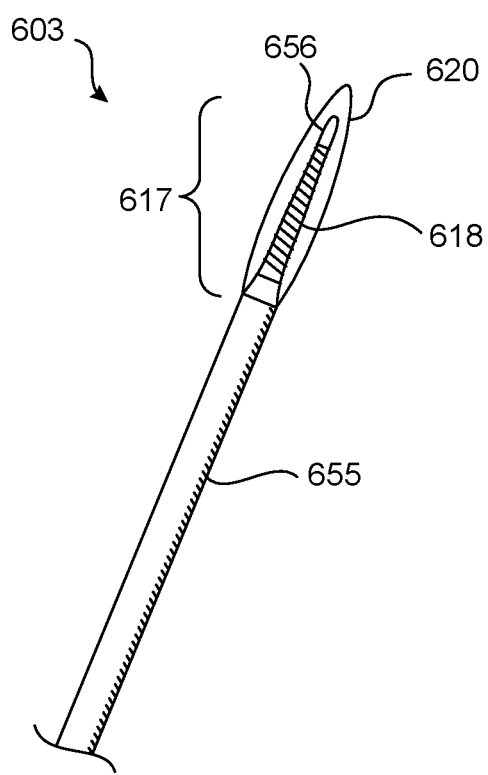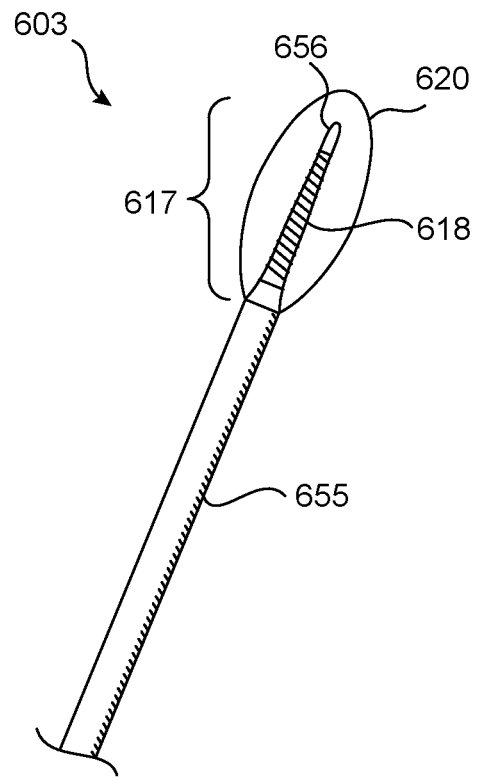
FIG. 6A  FIG. 6B

700

701
Inserting an energy delivery balloon catheter into the vasculature of a patient, and navigating the catheter to the patient's heart with the balloon in a first, slimmer profile configuration

702
Positioning the energy delivery balloon catheter within the lumen of an actuatable portion of a cardiac shunt while the actuatable portion is in a first state associated with a first geometry

703
Inflating the balloon with an expansion medium such that the balloon expands into a second, larger configuration and applies a radial force to a relatively malleable component within the actuatable portion of the cardiac shunt, thereby enlarging a geometry of a section of a shunt in a manner that is reversible and increasing the flow potential therethrough

704
Deflating the balloon by removing expansion media and therefore reducing the size of the balloon relative to the second, larger configuration, and removing the catheter from the body in a manner that maintains the actuatable portion of the shunt in an increased-sized geometry relative to the first shunt state and shunt geometry

*FIG. 7*

800

801
Inserting an energy delivery balloon catheter into the vasculature of a patient, and navigating the catheter to the patient's heart with the balloon in a first, slimmer profile configuration

802
Positioning the energy delivery balloon catheter within the lumen of an actuatable portion of a cardiac shunt while the actuatable portion is in a firststate associated with a first geometry

803
Inflating the balloon with an expansion medium such that the balloon expands into a second, larger configuration and establishes contact with a shape memory component within the actuatable portion of the cardiac shunt

804
Applying heat to the shape memory component within the actuatable portion of the shunt via an energy source within or operably-coupled to the balloon, thereby raising the temperature of one or more sections of the shape memory component above a material state transition temperature and causing the shape memory component to move towards a preferred geometry and consequently changing the geometry of the actuatable portion of the shunt to a second geometry different than the first geometry

805
Deflating the balloon by removing expansion media and therefore reducing the size of the balloon relative to the second, larger configuration, and removing the catheter from the body in a manner that maintains the actuatable portion of the shunt in an altered geometry relative to the first shunt state and shunt geometry

901 Inserting an energy delivery balloon catheter into the vasculature of a patient, and navigating the catheter to the patient's heart with the balloon in a first, slimmer profile configuration

902 Positioning the energy delivery balloon catheter within the lumen of an actuatable portion of a cardiac shunt while the actuatable portion is in a first state associated with a first geometry

903 Inflating the balloon with an expansion medium such that the balloon expands into a second, larger configuration and establishes contact with a shape memory component within the actuatable portion of the cardiac shunt

904 Applying heat to the shape memory component within the actuatable portion of the shunt via an energy source within or operably-coupled to the balloon, thereby raising the temperature of one or more sections of the shape memory component above a material state transition temperature and causing the shape memory component to move towards a preferred geometry and consequently reducing the geometry of the actuatable portion of the shunt to a second geometry smaller than the first geometry

905 With the energy source deactivated, inflating the balloon with an expansion medium that is near or below body temperature such that the balloon expands into a configuration larger than the first, slimmer profile configuration and applies a radial force to the shape memory component within the actuatable portion of the cardiac shunt without raising the temperature of the shape memory component above a material state transition temperature, thereby deforming the relatively malleable shape memory component and enlarging a geometry of a section of a shunt to a geometry larger than the second shunt geometry, and consequently increasing the flow potential therethrough.

906 Deflating the balloon by removing expansion media and therefore reducing the size of the balloon relative to the second, larger configuration, and removing the catheter from the body in a manner that maintains the actuatable portion of the shunt in an altered geometry relative to the first shunt state and shunt geometry

*FIG. 9*

ADJUSTABLE IMPLANTABLE DEVICES AND ASSOCIATED METHODS

CROSS-REFERENCE TO RELATED APPLICATION(S)

This application is a continuation of U.S. application Ser. No. 17/524,631, filed Nov. 11, 2021, which claims the benefit of (a) U.S. Provisional Application No. 63/112,787, filed Nov. 12, 2020, and (b) U.S. Provisional Application No. 63/164,481, filed Mar. 22, 2021, the disclosures of which are both incorporated by reference herein in their entireties.

TECHNICAL FIELD

The present technology generally relates to implantable medical devices and, in various aspects, to invasive adjustment systems for such implantable medical devices and associated systems and methods.

BACKGROUND

Implantable medical devices are commonly employed for treating various conditions. For example, stents are used for treating blocked vessels, implantable sensors are used for monitoring physiological conditions, and prosthetics are used for replacing diseased or damaged parts of the body. Certain implantables have a limited life by virtue of their electronics and need to be replaced if the patient's needs outlast the effective life of the implantable device (e.g., pacemakers, defibrillators). Many types of implantables are passive, and thus useful for long term and/or permanent implantation.

An example of such devices are implantable shunting systems. Implantable shunting systems (e.g., cardiac shunts, cerebral shunts, etc.) can be used to create and/or control fluid flow between different parts of a patient's body, typically cavities and/or vessels. For example, interatrial shunts may be used to treat heart failure (HF) patients with elevated left atrial pressure, e.g., by decompressing the left atrium (LA) by relieving pressure to the right atrium (RA) and systemic veins. However, conventional shunts generally have an annular passage with a fixed diameter which fails to account for a patient's changing physiology and condition. For this reason, conventional shunt devices may have a diminishing clinical effect after a period of time. Many conventional shunt devices typically are also only available in a single size that may work well for one patient but not another. Also, sometimes the amount of shunting created during the initial procedure is later determined to be less than optimal months after implantation. Moreover, under conventional approaches, the clinician may not be able to assess the state of the implanted shunt without invasive procedures (e.g., invasive replacement or surgery). Accordingly, there is a need for improved devices, systems, and methods for shunting fluid within a patient's body.

BRIEF DESCRIPTION OF THE DRAWINGS

FIG. 2 is a block diagram illustrating a method for adjusting a medical system in accordance with embodiments of the present technology.

FIG. 3 is a block diagram illustrating a method for adjusting a medical system in accordance with another embodiment of the present technology.

FIGS. 6A and 6B illustrate a distal section of an energy delivery catheter configured in accordance with embodiments of the present technology.

FIGS. 7-9 are block diagrams illustrating methods for adjusting a medical system in accordance with embodiments of the present technology.

DETAILED DESCRIPTION

Figure 1:
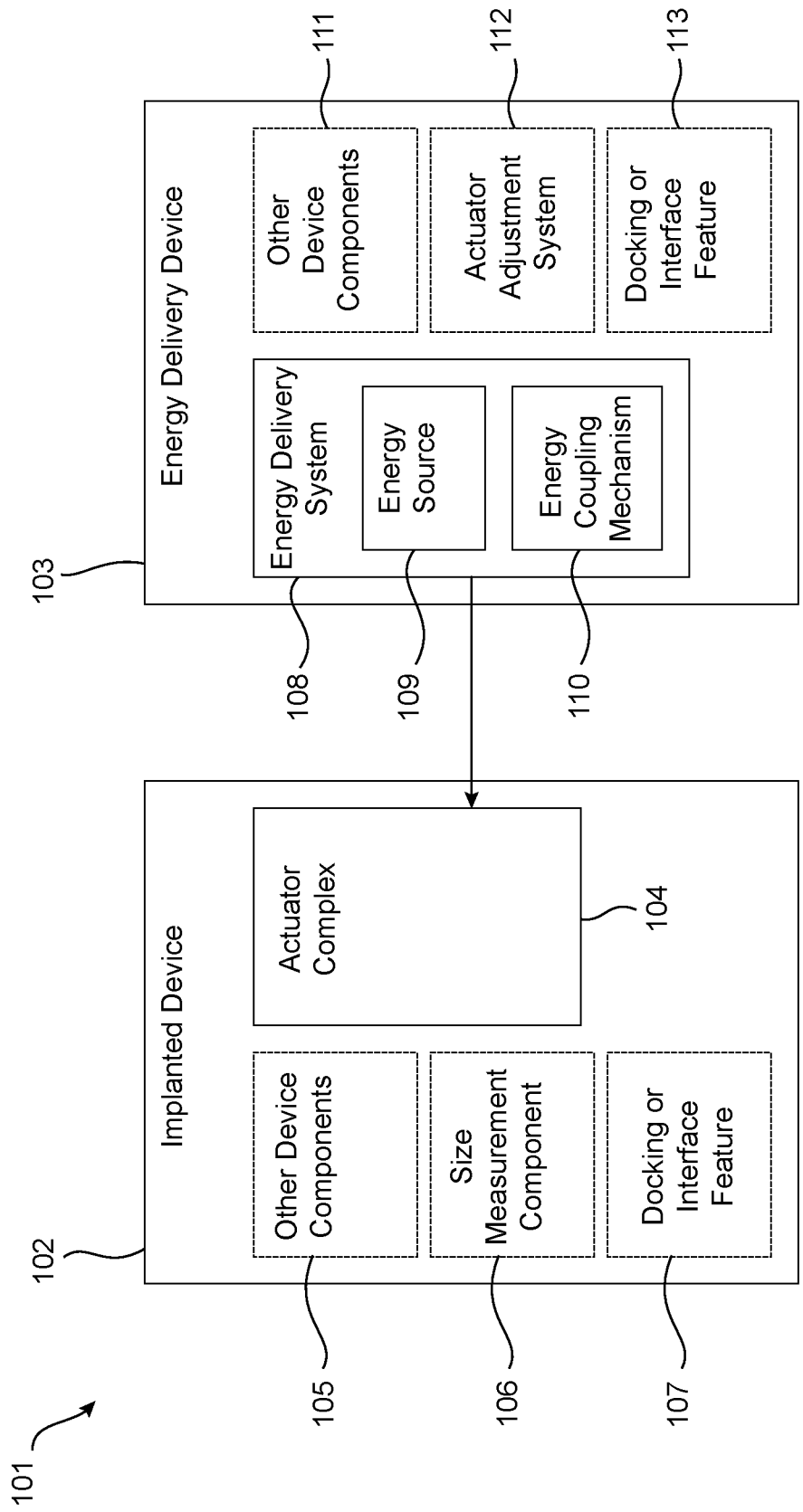
FIG. 1 is a simplified block diagram of a medical system configured in accordance with an embodiment of the present technology.

The present technology is generally directed to implantable medical devices and, in various aspects, to systems and methods for invasively adjusting implantable devices for selectively controlling fluid flow between a first body region and a second body region of a patient. For example, in many of the embodiments described herein, a catheter or other elongated body can be used to mechanically, thermally, and/or electrically engage an implanted medical device.

Once the catheter engages the medical device, the catheter can (i) increase a dimension associated with the medical device, such as through mechanical expansion forces, and/or (ii) decrease a dimension associated with the medical device, such as by heating a shape memory component of the medical device above a phase transition temperature.

For example, in some embodiments the present technology includes a system comprising a shunt configured to be implanted in a patient to fluidly couple the first body region and the second body region, and an energy delivery catheter configured to selectively adjust a dimension or parameter of the shunt. The shunt can include a flowpath that permits fluid to flow through the shunt between the first and second body regions. The shunt can also include an actuation section with a shape memory actuation component that is bi-directionally adjustable along at least one dimension. The catheter can include an expandable member for engaging the shunt, and one or more energy delivery elements configured to heat the shape memory component when the expandable member is in an expanded configuration. In some embodiments, the shape memory component, when heated via the one or more energy delivery elements, undergoes a material phase transformation that induces a geometric change in the shape memory component and changes a dimension of the flowpath.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-19.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

As used herein, the term "shunt" is used to refer to a device that, in at least one configuration, can provide a fluid flow (e.g., blood flow) between a first region (e.g., a LA of a heart) and a second region (e.g., a RA or coronary sinus of the heart) of a patient. Although certain embodiments herein are described in terms of a shunt between the atria, namely the left and right atria, one will appreciate that the technology may be applied equally to devices positioned between other chambers and passages of the heart, between other parts of the cardiovascular system, or other parts of a patient's body. For example, any of the shunts described herein, including those referred to as "interatrial," may be nevertheless used and/or modified to shunt between the LA and the coronary sinus, between the right pulmonary vein and the superior vena cava, or between other body regions. Moreover, while the disclosure herein primarily describes shunting blood from the LA to the RA, the present technology can be readily adapted to shunt blood from the RA to the LA to treat certain conditions, such as pulmonary hypertension. For example, mirror images of embodiments, or in some cases identical embodiments, used to shunt blood from the LA to the RA can be used to shunt blood from the RA to the LA in certain patients.

The headings provided herein are for convenience only and do not interpret the scope or meaning of the claimed present technology.

A. Select Embodiments of Systems and Methods for Selectively Adjusting Implantable Devices FIG. 1 is a simplified block diagram of a medical system 101 ("system 101") configured in accordance with an embodiment of the present technology. More specifically, system 101 is configured to enable bi-directional adjustment of a geometric dimension of an implantable device. In the figure, select components of the system 101 are denoted by solid boxes and optional system components are denoted by dashed boxes, although one skilled in the art will appreciate the system 101 can include any combination of the foregoing components. The system 101 can contain two main subsystem components, an implanted device 102 (e.g., a shunt, an occluder, a hemodynamic monitor, etc.) and an energy delivery device 103 (e.g., a catheter system, an energy delivery apparatus, an external transmitter, a subcutaneous implant, etc.). The implanted device 102 contains an actuator complex 104. The actuator complex 104 may be comprised of multiple components, at least one of which is bi-directionally adjustable along at least one dimension. In some implementations, the actuator complex 104 contains a component that has a radially-adjustable geometry (i.e., can be configured to change diameter, cross-sectional area, and/or another similar parameter).

Within examples, the implanted device 102 of system 101 can contain additional components or features. Some implementations may include a docking or interface feature 107 (e.g., a groove, notch, magnet, tether, or another interface known to those skilled in the art) intended to facilitate the coupling of the implanted device 102 with an energy delivery device 103. Implementations of the implanted device 102 may also include one or more size measurement components 106 intended to measure and/or transmit/display a geometric dimension associated with the actuator complex 104. The implanted device 102 may optionally be comprised of additional device components 105, which in examples may include anchoring or stabilization features, structural components such as frames or scaffolds, sensing or diagnostic components, electronic components, or other components known in the art.

The system 101 also contains an energy delivery device 103 intended to interface with the implanted device 102 at a time following the initial implantation/placement of the device. The energy delivery device 103 contains an energy delivery system 108 which is capable of conveying energy to the actuator complex 104 of the implanted device 102. Within examples, the energy delivery system 108 is comprised of at least two components: an energy source 109 and an energy coupling mechanism 110 which facilitates the transmission of energy from the energy source 109 to the actuator complex 104. In some implementations the energy source 109 and energy coupling mechanism 110 may take the form of a single component. In variation implementations the energy coupling mechanism 110 may be omitted and the energy source 109 may interface with the actuator complex 104 directly. In some implementations, the energy delivery system 108 may contain additional components (e.g., various electrical components and/or mechanical controls). The energy delivery system 108, whether composed of a single component or multiple components, can also be referred to herein as an energy delivery device and/or an energy delivery element.

Within examples, the energy delivery device 103 may contain additional components or features. Some implementations may include a docking or interface feature 113 (e.g., a groove, notch, magnet, tether, or another interface known to those skilled in the art) intended to facilitate coupling to the implanted device 102. The docking or interface feature 113 may be stand-alone or may form a portion of an interface complex with a complementary docking or interface feature 107 that is located on the implanted device 102. Implementations of the energy delivery device 103 can also include one or more actuator adjustment systems 112 that are intended to alter the geometry of at least a portion of the actuator complex 104 without the use of the energy source 109. Within examples, the actuator adjustment system 112 may be co-located or integral with an energy delivery system 108. In implementations, an energy delivery device 103 may contain an actuator adjustment system 112 and an energy delivery system 108 that work complementary to one another; for example, the energy delivery system 108 may adjust a geometry of the actuator complex 104 in a first direction and the actuator adjustment system 112 may adjust the actuator complex 104 in a second direction that is different than the first direction. In some implementations, the changes in actuator complex 104 geometry induced by the energy delivery system 108 may be reversed by the actuator adjustment system 112, and/or vice-versa.

The energy delivery device 103 can be comprised of additional device components 111, which in selected implementations may include guidewires, sheaths, steering components, handles, buttons, switches, toggles and other user interface features, power sources, lumens, injection ports, sensors and related electronics, imaging components, or other components known in the art.

FIG. 2 is a block diagram illustrating a method ("method 200") for adjusting a medical system in accordance with embodiments of the present technology. The method 200 can be utilized in conjunction with system 101 (FIG. 1) or other suitable medical systems. Beginning at step 201, the method 200 can involve interfacing an energy delivery device (e.g., device 103) with an implanted medical device (e.g., device 102). A second step 202 can involve using an energy delivery system (e.g., system 108) on the energy delivery device to adjust a geometry of an actuator complex (e.g., complex 104) on the implanted device from a first geometry to a second geometry in a manner that is reversible (e.g., an adjustment that makes part of an actuator complex smaller can later be undone, returning the part of the actuator complex to its larger pre-adjustment size). A third step 203 can involve decoupling the energy delivery device from the implanted medical device in a manner such that actuator complex remains in a geometry that is altered from the first geometry, and removing the energy delivery device from the body.

FIG. 3 is a block diagram illustrating a method ("method 300") for adjusting a medical system in accordance with another embodiment of the present technology. The method 300 can be utilized in conjunction with system 101 (FIG. 1) or other suitable medical systems. Beginning at step 301, the method 300 can involve interfacing an energy delivery device (e.g., device 103) with an implanted medical device (e.g., device 102) that includes an actuator complex (e.g., complex 104) having an initial geometry. A second step 302 can involve using an energy delivery system (e.g., system 108) on the energy delivery device to adjust a dimension of the actuator complex on the implanted device in a first direction. In some embodiments, the second step 302 includes adjusting a dimension of the actuator complex in a first direction to and/or toward a minimum dimension. A third step 303 can involve using the energy delivery device to make a second adjustment of a dimension of the actuator complex on the implanted device in a second, opposite direction. In some implementations of the method, steps 302 and 303 may be repeated multiple times (e.g., subsequently performed back and forth to arrive at a desirable geometry before proceeding to an additional step). A fourth step 304 can involve decoupling the energy delivery device from the implanted medical device in a manner such that actuator complex remains in a geometry that is altered from the initial geometry, and removing the delivery device from the body. Method 300 takes advantage of the novel bi-directional adjustment features enabled by the present technology described herein. An advantage of method 300 is that it can allow for more precise adjustments of a dimension of a medical device by always returning to a known actuator geometry (e.g., via step 302, returning an actuator to a minimum dimension) prior to making a subsequent adjustment. An additional advantage of method 300 is that a geometry of an implanted device can be both compressed or enlarged, which is not generally possible with current devices known in the art.

Figure 4:
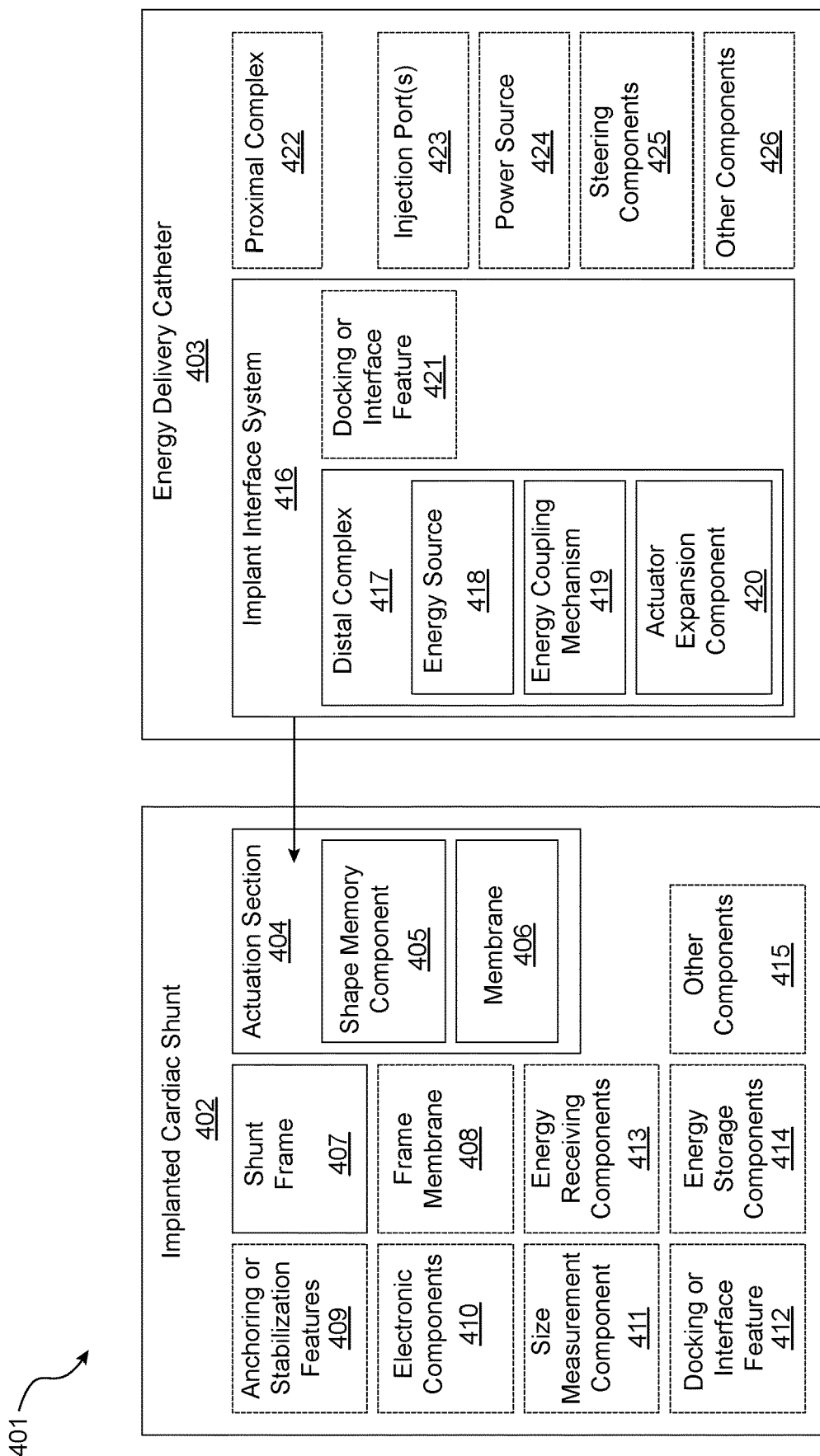
FIG. 4 is a simplified block diagram of a medical system including an implantable cardiac shunt and an energy delivery catheter device configured in accordance with an embodiment of the present technology.

FIG. 4 is a simplified block diagram of an implementation that may be instituted in connection with system 101, according to examples of the present disclosure. More specifically FIG. 4 illustrates a simplified block diagram of a medical system 401 ("system 401") that includes an implantable cardiac shunt 402 (e.g., an interatrial shunt) and a catheter device 403 (e.g., an elongated energy delivery catheter) configured to interface with the implanted shunt at a time during or following implantation. Though not shown, system 401 may contain additional components and subsystems, for example a delivery catheter device for initial implantation of the device into the body of a patient. In the figure, select components of the system 401 are denoted by solid boxes and optional system components are denoted by dashed boxes, although one skilled in the art will appreciate the system 401 can include any combination of the foregoing components. It should be understood that any components of system 401 can be present in any number of quantities. For example, there may be a single instance of a component or a plurality of the component, regardless of how the component is described in FIG. 4.

An implanted cardiac shunt 402 can be utilized to fluidly connect two regions of the cardiovascular system, for example two chambers of the heart. For example, the shunt may be an interatrial shunt that is implanted on to or into the atrial septum to fluidly connect the left atrium (LA) and right atrium (RA). An implementation of the cardiac shunt 402 includes a frame 407 that provides structure to the device and, in some examples, interfaces with a septal wall. The frame 407 may have a lattice or stent-like design and be comprised of a biocompatible material such as nitinol, stainless steel, a polymer, or other materials known to those skilled in the art. The frame 407 may hold a hole or opening that has been created in a septal wall patent and in a fixed geometry and therefore define at least a portion of the fluid communication pathway or orifice between the LA and the RA.

The cardiac shunt 402 can also include one or more frame membranes 408 that interfaces with the shunt frame 407 and optionally other aspects of the device. The frame membrane(s) 408 may line, envelop, or otherwise join with the frame 407 to establish a flow lumen between the LA and the RA. The membrane may be comprised of a material such as expanded polytetrafluoroethylene (ePTFE), polyethylene terephthalate (PET) (e.g., sold under the trademark DACRON), polycarbonate urethane, silicone, nylon, latex, or another material. In applications, it may be desired for the membrane material to be biocompatible, non-thrombogenic, substantially fluid impermeable, elastic/flexible, and resistant to damage, tearing, wear, etc. The cardiac shunt 402 can also include anchoring or stabilization features 409 that help maintain the position of the device, for example to keep the shunt attached to, integrated into, or otherwise interfaced with the septal wall. Anchors may take the form of spirals, tines, coils, meshes, or other features that are integral to or attach to the frame 407 and interface with tissue in the region of implantation. Stabilization features may be used to hold the cardiac shunt 402 in place without applying meaningful forces to a septal wall, and may take the form of flared or trumpeted sections of the device that become larger in diameter than the septal opening, thereby preventing portions of the deployed device from migrating back through the septal opening to an undesired location. Within examples, there may be a plurality of anchoring or stabilization features 409, for example features on both the LA and RA sides of a septal wall. In such implementations, a first anchoring or stabilization feature may differ from additional anchoring or stabilization features found elsewhere on the cardiac shunt 402.

The cardiac shunt 402 also includes an actuation section 404 that is bi-directionally adjustable along at least one dimension. Within examples, the actuation section 404 includes both a shape memory component 405 and a membrane 406. In some implementations, the membrane 406 may be similar to, identical to, or contiguous with frame membrane 408. The shape memory component 405 may be comprised of nitinol or a similar metallic alloy or polymer that has been manufactured to have a material phase transition or glass transition temperature (e.g., an austenite start temperature, an austenite finish temperature, etc.) that is higher than body temperature. As described in detail in the examples provided below, the shape memory component 405 is configured to be adaptable to a plurality of geometric configurations, and can be adjusted bidirectionally (i.e., in at least one dimension, it can be both increased from a smaller geometry to a larger geometry and decreased from a larger geometry to a smaller geometry). In implementations, the shape memory component 405 can be adjusted radially and therefore a diameter of a generally circular or ovular cross-section defined by the shape memory component can be altered. In implementations, some geometric adjustments (e.g., those below the plastic strain limit) to the shape memory component 405 are reversible (e.g., after the shape memory component has been adjusted from a smaller geometry to a larger geometry, it can be further adjusted to regain the smaller geometry). Within examples, the membrane 406 can be utilized to give structure to the actuation section 404 of the cardiac shunt 402, defining the fluid transmission pathway through this section 404. In implementations, the membrane 406 can be utilized as a means to mechanically join the actuation section 404 to the shunt frame 407. In other implementations, the membrane 406 may serve as part of a complex that mechanically joins or otherwise operably couples the actuation section 404 to the shunt frame 407. In some implementations, the shunt frame 407, frame membrane 408, and actuation section 404 define substantially the entire fluid transmission pathway created by the cardiac shunt 402. As such, changing the geometry of actuation section 404 corresponds with an alteration of the fluid transmission that occurs through conduit between the heart regions that is created by the shunt 402.

Within examples of system 401, the implanted cardiac shunt 402 can optionally include additional components and features. The shunt 402 can integrate various electronic components 410, which may include one or more sensors, microcontrollers, ASICs, FPGAs, and/or other components known to those skilled in the art. The implanted cardiac shunt 402 can integrate one or more energy receiving components 413 that are capable of receiving a signal from a source external to the cardiac shunt 402. The receiving components 413 can include induction coils, piezoelectric receivers, antennas, other energy receiving coil(s), and/or other components known to those skilled in the art. In implementations, the one or more energy receiving components 413 are adapted to further relay received energy to other components (e.g., electronic components 410) and thus can be used as a means to provide the implanted cardiac shunt 402 with electrical power. This power can be utilized to enable and/or augment the operation of sensors, microcontrollers, and/or other device components. The implanted cardiac shunt 402 may optionally integrate one or more energy storage components 414 (e.g., a battery, a supercapacitor, a capacitor, etc.). The energy storage components 414 may provide electrical energy to enable operation of sensors, microcontrollers, and/or other device components. Some implementations of the cardiac shunt 402 may contain both energy receiving components 413 and energy storage components 414. In some such implementations, the energy receiving components 413 and energy storage components 414 can work in tandem to provide electrical power to electrical components 410. In some implementations, energy receiving components 413 can be utilized to capture energy which is transferred to and subsequently stored in energy storage components 414.

Within examples of system 401, the implanted cardiac shunt 402 includes a size measurement component or system 411. The size measurement component or system 411 can take a spectrum of forms (e.g., sensors, visual markers, electrical circuitry, etc.) appropriate to the structure of actuation section 404, and is utilized to provide quantitative and/or qualitative (e.g., actuation section 404 is in a relatively larger state than previously, actuation section 404 is in a relatively smaller state than previously, etc.) information to a user (e.g., a patient, a physician, a care provider) regarding the geometric configuration of the actuation section 404 at a moment in time. Implementations of an implanted cardiac shunt 402 may also include a docking or interface feature 412 (which can be substantially identical to the docking or interface feature 107 described above as part of system 101) that may be utilized to facilitate the coupling of energy delivery catheter 403 with the implanted cardiac shunt 402. Within examples the shunt 402 may optionally contain other components 415 not explicitly described herein (e.g., radiographic markers, material components, bioabsorbable components or layers, etc.).

Referring to FIG. 4, the system 401 includes an energy delivery catheter 403 or other elongated body that is adapted to interface with the cardiac shunt 402 at a time following its implantation into the body of a subject. The energy delivery catheter 403 includes an implant interface system 416, which in examples is a subsystem of the catheter adapted to mechanically and/or energetically couple with the cardiac shunt 402. In examples the implant interface system 416 is located at or near the distal end of catheter 403. In examples, the implant interface system 416 interfaces directly with the actuation section 404 of the implanted shunt 402. In some implementations, the implant interface system 416 contains a docking or interface feature 421 which facilitates coupling of the energy delivery catheter 403 to the implanted cardiac shunt 402. In some embodiments, this docking or interface feature 421 can be substantially identical to the interface feature 113 described above in accordance with system 101. In implementations of system 401, the docking or interface feature 421 mates with, interfaces with, or works in conjunction with a docking or interface feature 412 on the implanted cardiac shunt 402. In alternate implementations, the docking or interface feature 421 independently facilitates coupling of the energy delivery catheter 403 to the implanted cardiac shunt 402, irrespective to the functionality of or presence of a docking or interface feature 412 located on the cardiac shunt 402. In some implementations of system 401, no docking or interface feature 421 is present on the energy delivery catheter 403.

The implant interface system 416 of energy delivery catheter 403 also includes a distal complex 417 located at or near the distal end of the energy delivery catheter. The distal complex 417 can contain components adapted to interface with the actuation section 404 and alter at least one geographic dimension of the actuation section 404 bi-directionally (i.e., the distal complex can be utilized to both enlarge or reduce a dimension of the actuation section). In the example shown, the distal complex 417 includes an actuator expansion component 420 that is used to enlarge or expand one or more components (e.g., the shape memory component 405) that comprise the actuation section 404. Within examples, the actuator expansion component 420 can alter a geometry of an actuation section 404 without using energy from an energy source 418 (described below). In examples, the actuator expansion component 420 is a balloon (e.g., a compliant balloon, a semi-compliant balloon, a non-compliant balloon, etc.) adapted to dilate a shape memory component 405 via a balloon expansion. In such examples, the actuator expansion component 420 may be comprised of a balloon constructed from polyurethane, silicone, polyether block amide (sold under the trademark PEBAX), latex, polyester, nylon, or other materials known to those skilled in the art and mounted to a central shaft with an inflation port. The expansion component 420 may be transitionable from a first (e.g., collapsed) configuration to a second (e.g., expanded) configuration by a user, for example by using a syringe coupled to a proximal complex 422 (described below) that resides at or near the proximal end of the energy delivery catheter 403 to inject an expansion medium (e.g., a fluid, gas, foam, etc.) into the balloon via a lumen in the catheter shaft (not shown in FIG. 4). When positioned such that it is mechanically coupled to the shape memory component 405 and/or actuation section 404 (e.g., via docking or interface feature 412 and/or 421), transitioning the actuator expansion component 420 from the first configuration to the second configuration can apply a mechanical force to shape memory component 405 which causes this component to enlarge, expand, or otherwise transform geometry in a way that increases a geometric dimension of actuation section 404. In implementations, the shape memory component 405 may be in a first material state (e.g., a martensitic state, an R-phase state) at body temperature. In such implementations, the shape memory component 405 may be relatively malleable and thermo-elastic in this first material state, and thus be deformable/expandable by the mechanical forces applied by actuator expansion component 420. In implementations, the actuator expansion component 420 is not significantly above body temperature (e.g., at or within 5 degrees Celsius of body temperature) when it applies mechanical forces to shape memory component 405. In implementations, the actuator expansion component 420 is below body temperature but above a temperature that may be harmful to tissue (e.g., between 0 degrees Celsius and body temperature), such that it can reduce the temperature of the shape memory component 405, thereby making shape memory component 405 further malleable relative to its material characteristics when at or near body temperature.

Alternative implementations of a medical system with a number of features similar to and/or substantially identical to systems 101 and 401 may utilize an actuator expansion component 420 that does not take the form of a balloon and/or that is not part of a distal complex 417. In examples, the actuator expansion component 420 is a metallic (e.g., stainless steel, titanium, etc.) cage that can expand (e.g., a radial expansion) from a slimmer delivery configuration to a larger implant interface configuration in respond to a user operating a control feature proximate to proximal complex 422 (described below). In examples, the actuator expansion component 420 can include one or more shape memory components that enable a geometry change (e.g., an expansion from a first, slimmer delivery configuration to a second, larger implant interface configuration) in response to the application of energy (e.g., heat) that results in the energy delivery catheter's shape memory component changing from a first material state (e.g., a martensitic state or an R-phase state) to a second material state (e.g., to an R-phase state or an austenitic state).

In examples, the actuator expansion component 420 is adapted such that it may also be configured by a user into one or more intermediate configurations between a first and second configuration, for example by inducing an intermediate degree of balloon expansion by injecting an intermediate volume of an expansion media into a balloon. In such examples, the distal complex 417 is capable of imparting a plurality of geometric alterations to the actuation section 404 based upon the relative degree of configuration change of the actuator expansion component 420.

The distal complex 417 of the energy delivery catheter 403 can also contain an energy source 418 and an energy coupling mechanism 419 (which can collectively or individually be referred to as an energy delivery device and/or energy delivery element). The energy coupling mechanism 419 may aid in the conveyance of energy from the energy source 418 to the actuation section 404 of the implanted cardiac shunt 402. The energy source 418 provides energy to system 401 that may be used to alter the geometry of actuation section 404 (e.g., to reduce the size of a dimension of the actuation section). Within examples, the energy source 418 provides energy that is coupled by the energy coupling mechanism 419 to the shape memory component 405 of actuation section 404, which can result in the shape memory component 405 changing geometry. Within examples, when the shape memory component 405 undergoes a geometry change in response to the application of energy from the distal complex 417, that geometry change primarily results in a decrease in a dimension (e.g., a narrowing of a diameter). In some implementations, the shape memory component 405 is comprised of nitinol or a nitinol-based alloy that is in a first material state (e.g., a martensitic state or an R-phase state) at body temperature, and the application of energy from the distal complex 417 raises the temperature of the shape memory component 405 above a material transition temperature such that it transitions to a second material state (e.g., an R-phase state or an austenitic state), thereby enabling a change of geometry of the shape memory component via a shape memory effect. More specifically, when the shape memory component 405 is in a first material state at body temperature, it can be relatively malleable or thermo-elastic and therefore be deformed away from a preferred geometry (e.g., a manufactured geometry, an original geometry, a heat set geometry, etc.). This deformation can result from a number of operations (e.g., manipulation of the shape memory component before or during implantation, expansion or other adjustment of the shape memory component using actuator expansion component 420 or another tool/method, etc.). As the shape memory component 405 is heated above a transition temperature and moves from a first material state to a second material state, it can actuate from a first (e.g., deformed) geometric configuration towards a second (e.g., a preferred) geometric configuration, thereby changing a size and/or shape of actuation section 404.

In some implementations of system 401, there may be more than one energy source component 418. In examples of such implementations, the plurality of energy source components may be similar or identical (e.g., multiple instances of a specific component or system). In further examples of such implementations, at least one energy source 418 varies from at least one other energy source used as part of the implant interface system 416 (e.g., a radiofrequency energy source used in concert with an ultrasonic energy source). Within examples of system 401, the actuation section 404 of the cardiac shunt 402 is only adjusted using mechanical forces and/or energy provided by the distal complex 417 and/or the energy delivery catheter 403. In such examples, other sources of mechanical or electrical energy associated with the system 401 (e.g., energy receiving components 413, energy storage components 414) are used exclusively in association with portions of the system not related to the actuation section 404 (e.g., electrical components 410, size measurement component 411, etc.). In alternate examples, the actuation section 404 of the cardiac shunt 402 is adjusted using a combination of mechanical forces and/or energy provided by the distal complex 417 and/or the energy delivery catheter 403 and other sources of force/energy associated with the system 401. In implementations, the energy source 418 and energy coupling mechanism 419 may be a single entity (i.e., a single aspect or component of the system serves both functions). Within examples, the energy source 418 can provide mechanical energy, electrical energy, thermal (e.g., hot or cold) energy, electromagnetic energy, acoustic energy, or other relevant forms of energy known to those skilled in the art.

Within examples of a distal complex 417, energy source 418 is comprised of one or more radiofrequency (RF) electrodes that receive RF energy from a generator located elsewhere in system 401 (e.g., via a power source 424 located in proximal complex 422 or external to the energy delivery catheter 403). In some implementations, RF electrodes may provide energy to actuation section 404 indirectly by heating an energy coupling mechanism 419 that serves as an intermediary medium that transfers the heat to the actuation section 404. For example, a distal complex 417 can include a balloon that may be filled with a fluid (e.g., saline) or other conductive media such that it expands to contact at least a portion of actuation section 404. The distal complex 417 may include internal RF electrodes that heat the filling media, which serves as an energy coupling mechanism 419 to transfer the heat to the actuation section 404. In alternate implementations, RF electrodes may provide energy to actuation section 404 directly. For example, a distal complex 417 may include an expandable section (e.g., a balloon, a metallic cage, etc.) that is adapted such that when it is in an expanded state it contacts at least a portion of actuation section 404. The expandable section may include RF electrodes at or near the exterior of the section, such that actuation section 404 is heated directly. In such an implementation, the energy source 418 and energy coupling mechanism 419 may take the form of the same component.

Within alternate examples of distal complex 417, energy source 418 may be an energized media that is directed by energy delivery catheter 403 to the distal complex 417. For example, energy source 418 may be a pre-heated or pre-cooled liquid, gas, or foam that is energized remote from the distal complex 417 (e.g., via a power source 424 located in proximal complex 422 or external to the energy delivery catheter 403) and directed to the distal complex 417 through lumens, ports, or other aspects of energy delivery catheter 403. In some implementations, an energized media could be further energized (e.g., reheated or additionally heated) by one or more supplemental energy sources 418 located along aspects of the catheter (e.g., in the distal complex 417, along the catheter shaft, etc.). It will be clear to a skilled artisan that additional implementations of energy source 418 and energy coupling mechanism 419 are possible without loss of novelty.

Referring to FIG. 4, the energy delivery catheter 403 that is part of system 401 can further include a proximal complex 422 that can include a catheter handle or handpiece intended to be held by a user during operation. The proximal complex 422 may include various user control features that enable the operator to perform actions related to catheter operation (e.g., steering operations, energy delivery operations, fluid/contrast injection operations, etc.). Control features can include various dials, triggers, buttons, knobs, pulleys, switches, and other control features known to those skilled in the art. The handle can be comprised of plastic or other polymer or metallic materials, or combinations of these materials.

Some examples of an energy delivery catheter 403 that is part of system 401 can further include additional features. Some implementations may feature one or more injection ports 423, for example a port that can interface with a syringe (not shown) to inject media into the catheter (e.g., an energy source media, a saline flush, a balloon inflation media, a contrast agent, etc.). Some implementations may contain one or more power sources 424. A power source 424 can be used to provide energy to various aspects of catheter 403 (e.g., aspects related to energy source 418, aspects related to steering or navigation of the catheter, aspects related to lighting or illumination features, aspects related sensing and diagnostics, aspects related to functionality of electronics in the handle, etc.). The power source 424 can be a battery, a capacitor, a generator integral with or operably coupled to the catheter, an ultrasonic transducer, or other sources of power known to those skilled in the art. Some implementations of an energy delivery catheter 403 may contain steering components to aid in navigation of the catheter in and around target anatomy. Steering components may be comprised of pull wires, robotic components (e.g., those powered via power source 424), or other assemblies known to those skilled in the art. Some implementations of the catheter 403 may contain other various components 426, which could include the catheter body and/or shaft, one or more lumens, guidewires and/or sheaths, contrast or fluid ejection ports, illumination features, radiographic markers, sensors and diagnostics, and/or other components. Moreover, although described as a catheter 403, the catheter 403 can alternatively or additionally comprise a sheath, guidewire, dilator, or other elongated body configured to extend through the patient's vasculature and interface with the shunt 402 (the foregoing can be collectively referred to as an "elongated body" or an "energy delivery apparatus").

Figure 5A:
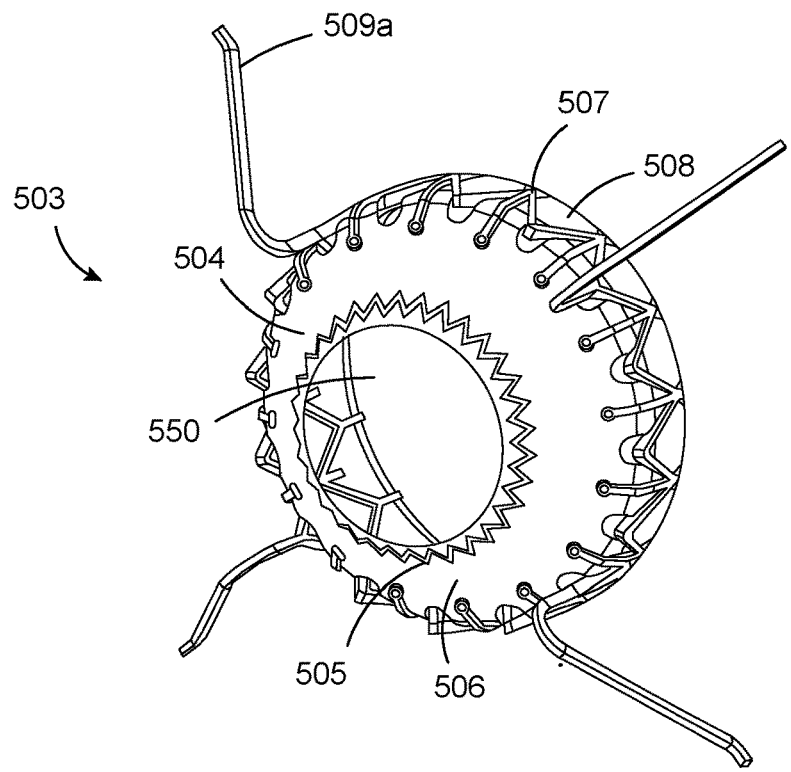
FIGS. 5A-5D illustrate an implantable interatrial cardiac shunt configured in accordance with an embodiment of the present technology.
Figure 5B:
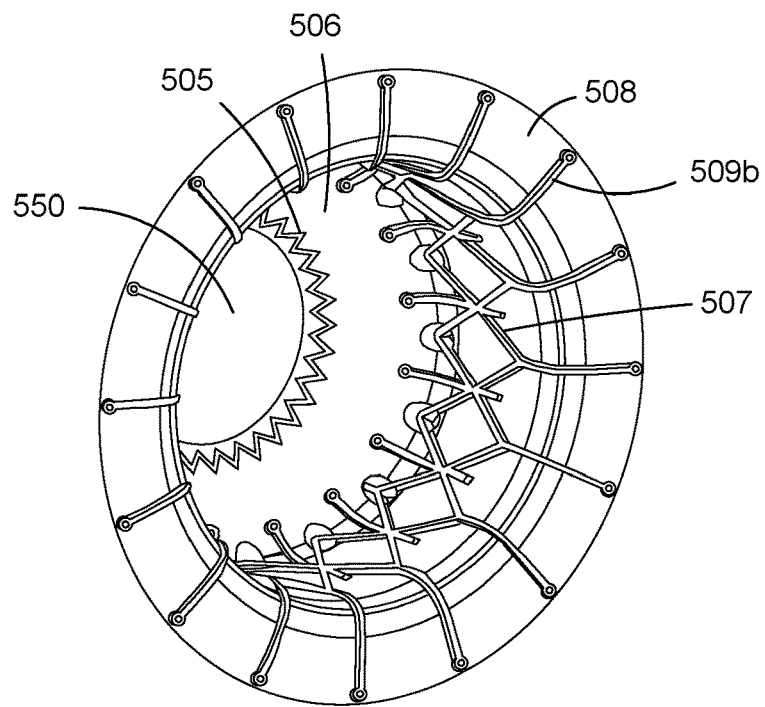
Figure 5C:
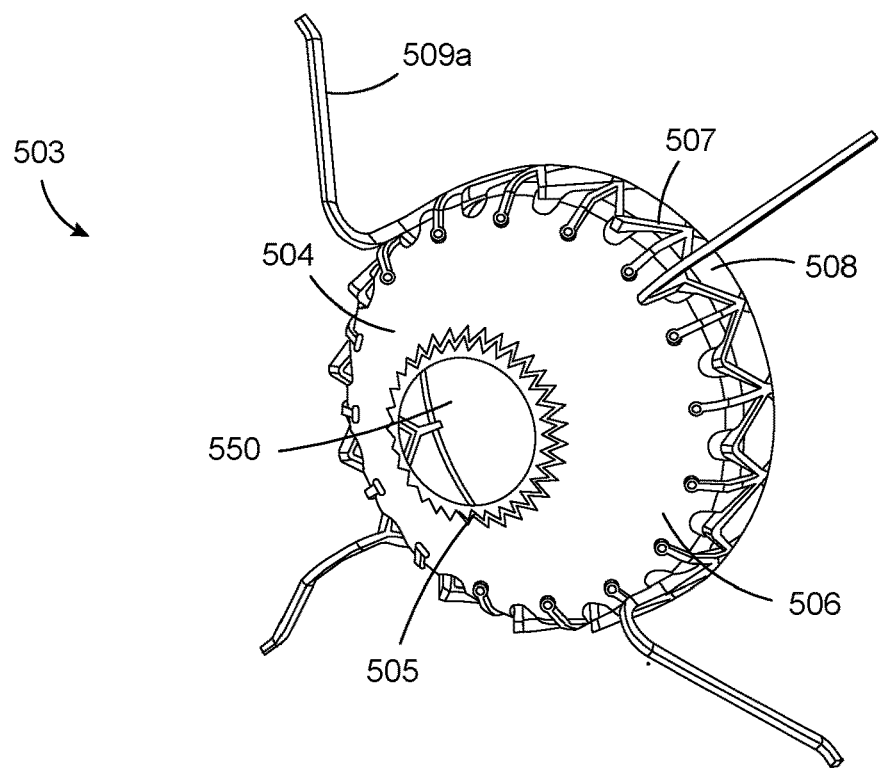
Figure 5D:
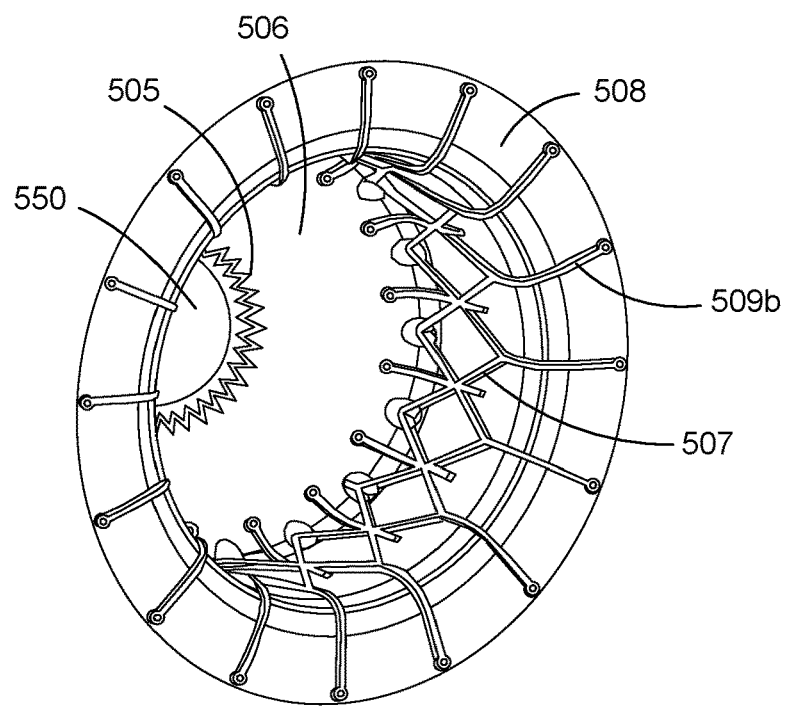

FIGS. 5A-6B show a plurality of implementations that can be instituted in connection with the medical systems 101 and 401 shown in FIGS. 1 and 4, respectfully, according to examples of the present disclosure. FIGS. 5A-5D, for example, illustrate an implantable interatrial cardiac shunt 503 configured in accordance with an embodiment of the present technology. FIGS. 5A and 5C show the shunt from a first partially isometric view as the shunt would be seen from inside the RA of a patient, while FIGS. 5B and 5D show a second partially isometric view featuring the opposite side of the shunt, as it would be seen from inside the LA of a patient. In FIGS. 5A and 5B, the shunt is shown in a first, relatively more open configuration, with an actuation section in a larger or expanded state. In FIGS. 5C and 5D, the shunt is shown in a second, relatively more closed configuration, with an actuation section in a smaller or contracted state.

In the illustrated embodiment, the cardiac shunt 503 includes an actuation section 504 having a shape memory component 505 and a membrane 506, a shunt frame 507, and a frame membrane 508, among other features. As shown, cardiac shunt 503 has a body defined by frame 507. Frame 507 can have a metallic structure and be self-expanding (e.g., if comprised of nitinol manufactured to exhibit superelastic properties at body temperature) or balloon expandable (e.g., if comprised of stainless steel, if comprised of nitinol manufactured to be largely martensitic at body temperature, etc.). As shown, frame 507 is mechanically-connected to a plurality of RA side anchoring elements 509a and a plurality of LA side anchoring elements 509b. In various examples, any number of anchoring elements may be utilized, and anchoring elements may take on various forms as described above. In implementations, the frame 507 and anchors 509 are a unibody that has been manufactured to self-deploy into the desired configuration during implantation (e.g., when released from a sheath or catheter, as known to those skilled in the art). In variation implementations, the frame 507 may be joined to anchoring elements 509 during manufacturing (e.g., using adhesives, welds, rivets, sutures, and the like). In some implementations, frame 507 may be joined to anchoring elements 509 via the membrane 508 (described below). Within examples, the frame 507 may join to a first set of anchoring elements (e.g., to elements 509a) using a first joining method and may join to a second set of anchoring elements (e.g., to elements 509b) using a second, different joining method.

In the example shown, anchoring elements 509a and 509b are intended to interface with a septal wall (not shown) to stabilize the position of the cardiac shunt 503. In examples, LA-side anchoring elements 509b may be relatively smaller and flat in order to reduce thrombogenicity in the left heart. In examples, RA-side anchoring elements may be relatively larger and have a shape and a flexibility to accommodate septal wall thickness variations that can be encountered in different portions of the septum and among different patients. In some implementations, coil-like anchoring elements may be implemented in order to address anatomical variations while also maintaining a relatively flatter profile, which may accelerate tissue overgrowth of the elements and further reduce risk of thrombus.

Cardiac shunt 503 can also contain a frame membrane 508 that can be operably-coupled to frame 507 and to LA-side anchoring elements 509b. In variation implementations, membrane 508 may alternatively or additionally be coupled to RA-side anchoring elements 509a. As shown, frame membrane 508 is affixed to an exterior surface of frame 507 and anchoring elements 509b. The fixation can be accomplished using various techniques known in the art (e.g., using adhesives, electrospinning of the membrane material, melting of the material onto the frame, suturing, interlocking components, etc.). Membrane 508 can be affixed to the frame 507 in any number of arrangements. For example, in variation implementations, membrane 508 can be affixed to an interior surface of the frame 507 and/or anchoring elements 509. In further variations, the frame 507 and/or anchoring elements may be sandwiched between multiple layers of membrane 508. In such variations that utilize multiple membrane layers, the material comprising the membrane on a first side of the frame 507 (e.g., an internal side) may differ from the material comprising the membrane on a second side of the frame 507 (e.g., an external side). This may be done to optimize performance of the implant—for example on the internal surface of the frame a membrane material can be selected to optimize for blood flow considerations, while on the external surface of the frame a membrane material can be selected to optimize for tissue response (e.g., to reduce any inflammatory response of septal tissues).

Cardiac shunt 503 further contains the actuation section 504 defined as the complex of the actuation section membrane 506 and the shape memory component 505. The actuation section 504 in this example is located on the RA side of the shunt, but in variation implementations can be located elsewhere on the implanted shunt device 503. The actuation section 504 can have a conical or tapered shape and include an opening or aperture 550 that defines the exit path for fluid traveling from the LA to the RA through the shunt. Together with the frame 507 and frame membrane 508, the actuation section 504 defines a lumen or fluid passageway that blood can travel therethrough. While the size and shape of the portion of the lumen defined by the frame 507 and frame membrane 508 remains constant or substantially constant through all operational states following implantation of the cardiac shunt 503, as described below the portion of the lumen defined by the actuation section 504 may vary in response to user/provider actions. As such the flow rate through cardiac shunt 503 can be altered by adjusting the actuation section 504 into different configurations.

In some implementations, portions of the shunt frame 507 can provide additional structural support to aspects of the actuation section 504. For instance, within examples elongated extensions of frame 507 can interface with actuation section membrane 506 to provide shape and structural integrity to this section. In said examples, these extensions of the frame 507 may be flexible in nature in order to accommodate changes in geometry of the actuation section 504. In variation implementations, the actuation section 504 may alternatively or additionally have other structural support (not shown), for example a lattice structure embedded into or otherwise coupled to the actuation section membrane 506.

Within examples, the actuation section membrane 506 can be identical to, similar to, or contiguous with frame membrane 508. In alternate examples, the actuation section membrane 506 may be constructed of a different material than frame membrane 508. In general, actuation section membrane 506 should be relatively fluid impermeable, relatively non-thrombogenic, and have some degree of flexibility to facilitate geometry changes associated with this section of the shunt. In examples, it may be constructed of silicone, ePTFE, nylon, a polyurethane, another polymer, or another appropriate material. In implementations, frame membrane 508 and actuation section membrane 506 are joined, fixed, or otherwise interfaced such that a continuous, relatively leak-free fluid pathway is created along the lumen defined by the cardiac shunt 503.

The actuation section membrane 506 is integral with shape memory component 505, and can be affixed to the exterior surface of component 505, affixed to the interior surface of component 505, be comprised of multiple layers that surround component 505, or be coupled in some combination of these ways or in a different way. Accordingly, as the shape memory component 505 changes in geometry, it can induce a change in geometry of the membrane. This geometry change may take the form of a stretching/relaxation of the membrane, a change in position (e.g., a change in angle of the membrane relative to shunt frame 507), some combination of these forms, or another form. As shown in FIGS. 5A-5D, the shape memory component 505 is configured as a ring with a zig-zag pattern. Such a pattern allows for radial expansion (i.e., a widening or opening of aperture 550, for example producing the configuration of FIGS. 5A-5B) and radial compression (i.e., a narrowing or closing of aperture 550, for example producing the configuration of FIGS. 5C-5D) of the shape memory component 505 to occur by inducing thermo-elastically recoverable deformations. This is an important feature which allows for repeated bi-directional adjustment of the actuation section (and therefore the shunt lumen, which governs flow through the shunt), as described in detail below.

FIGS. 6A and 6B illustrate a distal section of an energy delivery catheter 603 configured in accordance with embodiments of the present technology. In particular, FIG. 6A shows a view of the catheter with a distal complex 617 in a first, slim-profile configuration. FIG. 6B shows a view of the catheter with a distal complex 617 in a second, relatively expanded configuration. FIGS. 6A and 6B show example implementations of a distal complex 617 that features an energy source 618, an energy coupling mechanism 419 (FIG. 4), and an actuator expansion component 620, among other features. For clarity, the proximal portions of catheter 603 (which can include a proximal complex, power source, and other features) are not shown in the figures. However, as described below, these components are present within examples of the present technology.

Energy delivery catheter 603 includes a catheter body or shaft 655 that connects its proximal portions and distal portions (e.g., distal complex 617). The catheter body 655 is an elongated and flexible structure and may be comprised of various materials (e.g., silicone, polyurethane, polyethylene, polyvinylchloride, PTFE, nylon, etc.) known to those skilled in the art. The catheter body 655 can contain a plurality of lumens, for example lumens to accommodate the use of a guidewire (not shown), lumens to allow a media (e.g., an expansion media) to move between proximal and distal aspects of the catheter, and/or other lumens.

The distal complex 617 can be adapted to interface with the actuation section of an implanted medical device (e.g., cardiac shunt 503). The distal complex 617 can include an expandable balloon 620 that may be expanded from a first slimmer configuration (e.g., as shown in FIG. 6A) to a second larger configuration (e.g., as shown in FIG. 6B) by filling the balloon with an expansion medium (e.g., a fluid, gas, foam, etc.). Removing all or some of the expansion media from the balloon 620 can reverse the expansion and/or reduce the size of the balloon. Within examples, a dimension of the balloon 620 can also be reduced in size without removing media from its interior (e.g., if a compressive force is applied to the balloon that induces a shape change in the balloon via a transverse strain or expansion related to the Poisson effect). Expansion media can be transmitted into or out of the balloon by an operator, for example by utilizing a syringe coupled to an input port on a catheter handle that is part of the proximal complex (not shown). In such an implementation, media injected into the catheter 603 via a syringe would travel though a lumen (not shown) in catheter body 655 and exit an outflow port 656 located inside the portion of distal complex 617 encompassed by the balloon 620. In implementations, the balloon expansion media is an electrically and/or thermally conductive media (e.g., saline). In implementations, the balloon expansion media may serve as an energy coupling mechanism (e.g., coupling mechanism 419) as described above.

As described above, the distal complex 617 of energy delivery catheter 603 can include an energy source 618, which in some embodiments can include at least one electrode 618 (e.g., an RF electrode) that is affixed to the catheter body in the region surrounded by balloon 620. The electrode 618 is electrically-coupled to a power source (not shown) that is located remote from the distal complex 617 (e.g., in a catheter handle, in a generator separate from the catheter 603, etc.), for example via electrical wires that travel through a lumen (not shown) in, or embedded within, the catheter body 655. When energized (e.g., via a user toggling a control feature on a catheter handle to enable a power source), the electrode 618 can transfer energy to surrounding media (e.g., saline that fills a balloon) and cause the surrounding media to elevate in temperature. These elevations in temperature may be subsequently transferred/coupled to structures located proximate to the heated media (e.g., to the actuation section of cardiac shunt 503). Within examples, the energy delivery catheter 603 can be constructed with the electrode 618 residing elsewhere in the system so long as the expansion media (e.g., saline) can be heated by the electrode. For example, electrode 618 may reside along the length of the catheter body 655 or within the proximal complex 422 (FIG. 4).

Within examples, an expandable balloon 620 on catheter 603 can include one or more perforations that allow an expansion media to be expelled into the environment. In such implementations, the number, size, and/or locations of the perforations can be configured such that expansion media is generally only expelled from the balloon once a pressure threshold has been reached (e.g., after filling sufficiently to shift the balloon to a larger configuration (i.e., as shown in FIG. 6B)). In implementations, the expansion media that is expelled can be energized as described above and therefore can serve as an energy source 418 (FIG. 4) and/or energy coupling mechanism 419 (FIG. 4). In such examples, the energized media may be expelled into regions surrounding balloon 620 (e.g., into regions surrounding an actuation section of cardiac shunt 503), which can facilitate the elevation of local temperatures. This may allow for more rapid energy transfer to an actuatable component, and may further facilitate actuation of a contracting component by removing at least some counterforce that would be applied by a non-perforated balloon in contact with an actuation element.

FIGS. 7-9 show a plurality of flowcharts of methods of use that can be instituted in connection with examples of the present disclosure. More particularly, FIGS. 7-9 provide flowcharts of methods of use that are substantially similar to method 200 and/or method 300 described above, and that can be instituted in connected with examples such as those shown in FIGS. 5A-6B.

A flowchart describing a method of use ("method 700") for adjusting a medical system that can be utilized in conjunction with the presently described technologies is shown in FIG. 7. Beginning at step 701, the method 700 can involve inserting an energy delivery balloon catheter (e.g., catheter 603) into the vasculature of a patient and navigating the catheter to the patient's heart with the balloon (e.g., balloon 620) in a first, slimmer profile configuration (e.g., as shown in FIG. 6A). A second step 702 can involve positioning the energy delivery balloon catheter within the lumen of an actuatable portion of a cardiac shunt (e.g., cardiac shunt 503) while the actuatable portion is in a first state associated with a first geometry. A third step 703 can involve inflating the balloon with an expansion medium such that the balloon expands into a second, larger configuration (e.g., as shown in FIG. 6B) and applies a radial force to a relatively malleable component (e.g., component 505) within the actuatable portion of the cardiac shunt, thereby enlarging a geometry of a section of the shunt in a manner that is reversible, and increasing the flow potential therethrough. A fourth step 704 can involve deflating the balloon by removing expansion media and therefore reducing the size of the balloon relative to the second, larger configuration, and removing the catheter from the body in a manner that maintains the actuatable portion of the shunt in an increased-sized geometry relative to the first shunt state and shunt geometry.

Method 700 may be useful if it is desired to temporarily enlarge a shunt lumen diameter while retaining the ability to reverse said enlargements. For example, a physician may want to enlarge the diameter of an interatrial shunt to further relieve LA pressure, but may be uncertain if the patient's right-heart function is sufficiently strong to handle the increased blood volume and load. Method 700 enables a physician to evaluate the patient's response to the new shunt configuration for a period of time (e.g., minutes, hours, days, weeks, months, etc.) without jeopardizing the ability to return the patient safely to the original configuration if the patient response is unsatisfactory for any number of reasons.

A flowchart describing a method of use ("method 800") for adjusting a medical system that can be utilized in conjunction with the presently described technologies is shown in FIG. 8. A step 801 can involve inserting an energy delivery balloon catheter (e.g., catheter 603) into the vasculature of a patient and navigating the catheter to the patient's heart with the balloon (e.g., balloon 620) in a first, slimmer profile configuration (e.g., as shown in FIG. 6A). A second step 802 can involve positioning the energy delivery balloon catheter within the lumen of an actuatable portion of a cardiac shunt (e.g., cardiac shunt 503) while the actuatable portion is in a first state associated with a first geometry. A third step 803 can involve inflating the balloon with an expansion medium such that the balloon expands into a second, larger configuration (e.g., as shown in FIG. 6B) and establishes contact with a shape memory component (e.g., component 505) within the actuatable portion of the cardiac shunt. A fourth step 804 can involve applying heat to the shape memory component within the actuatable portion of the shunt via an energy source (e.g., RF electrode 618) within or operably-coupled to the balloon, thereby raising the temperature of one or more sections of the shape memory component above a material state transition temperature and causing the shape memory component to move towards a preferred geometry and consequently changing the geometry of the actuatable portion of the shunt to a second geometry different than the first geometry. Within implementations, steps 803 and 804 can be iteratively performed multiple times (e.g., iteratively) to arrive at the desired shape of the actuator. A fifth step 805 can involve deflating the balloon by removing expansion media and therefore reducing the size of the balloon relative to the second, larger configuration, and removing the catheter from the body in a manner that maintains the actuatable portion of the shunt in an altered geometry relative to the first shunt state and shunt geometry.

Within examples, method 800 can be utilized to reduce a geometry of at least a portion of a shunt from a relatively larger size (e.g., diameter) to a relatively smaller size. In such examples, the shape memory component in the actuation section of the shunt has been deformed from a preferred geometry, and is configured in a geometry that is larger or expanded relative to the preferred geometry. Accordingly, as the shape memory component is heated in step 804, the shape memory component will contract as it moves towards its preferred geometry. Method 800 is useful because it provides care providers with a practical and reversible technique for making a shunt lumen smaller after the time of shunt implantation, a capability not available in present devices and not described in the prior art. Method 800 is also useful because such contractions in a lumen geometry are reversible (i.e., the shape memory component can be later expanded into a larger geometry, for example via method 700). A shunt lumen/fluid conduit that can be reduced in size at a time following implantation and can later be enlarged represents a substantial leap forward in medical care and unlocks new treatment paradigms that physicians may offer to their patients.

A flowchart describing a method of use ("method 900") for adjusting a medical system that can be utilized in conjunction with the presently described technologies is shown in FIG. 9. A step 901 can involve inserting an energy delivery balloon catheter (e.g., catheter 603) into the vasculature of a patient and navigating the catheter to the patient's heart with the balloon (e.g., balloon 620) in a first, slimmer profile configuration (e.g., as shown in FIG. 6A). A second step 902 can involve positioning the energy delivery balloon catheter within the lumen of an actuatable portion of a cardiac shunt (e.g., cardiac shunt 503) while the actuatable portion is in a first state associated with a first geometry. A third step 903 can involve inflating the balloon with an expansion medium such that the balloon expands into a second, larger configuration (e.g., as shown in FIG. 6B) and establishes contact with a shape memory component (e.g., component 505) within the actuatable portion of the cardiac shunt. A fourth step 904 can involve applying heat to the shape memory component within the actuatable portion of the shunt via an energy source (e.g., RF electrode 618) within or operably-coupled to the balloon, thereby raising the temperature of one or more sections of the shape memory component above a material state transition temperature and causing the shape memory component to move towards a preferred geometry and consequently reducing the geometry of the actuatable portion of the shunt to a second geometry smaller than the first geometry. A fifth step 905 can involve: with the energy source deactivated, inflating the balloon with an expansion medium that is near or below body temperature such that the balloon expands into a configuration larger than the first, slimmer profile configuration and applies a radial force to the shape memory component within the actuatable portion of the cardiac shunt without raising the temperature of the shape memory component above a material state transition temperature, thereby deforming the relatively malleable shape memory component and enlarging a geometry of a section of a shunt to a geometry larger than the second shunt geometry, and consequently increasing the flow potential therethrough. A sixth step 906 can involve deflating the balloon by removing expansion media and therefore reducing the size of the balloon relative to the second, larger configuration, and removing the catheter from the body in a manner that maintains the actuatable portion of the shunt in an altered geometry relative to the second shunt geometry.

In variations of method 900, steps 903 and 904 may be combined into a single step. For example, in an implementation of method 900 when an expansion media (e.g., saline) is heated remote from the distal complex (e.g., heated in the handle) and then delivered to the distal complex, the balloon can inflate to contact a shape memory component while simultaneously transferring heat from the energized expansion media to the shape memory component. In other variations of method 900, step 905 can be an optional step. Further variations of method 900 can contain an additional step that involves removing expansion media from the balloon between heating the shape memory element to cause a reduction in size via the shape memory effect and re-expanding the shape memory element to a larger size using a radial force (e.g., between steps 904 and 905). Including this optional additional step may offer at least two advantages: (a) it can ensure that any heated (i.e., heated relative to body temperature) media in the balloon is removed prior to the expansion step 905, thereby reducing the likelihood of unintentionally re-heating the shape memory element above a transition temperature; (b) it can increase the precision with which the expansion step 905 can enlarge a shape memory element to a known size, given that the volume of expansion media in the balloon during step 905 may be more precisely known using this methodology.

Method 900 is useful because it can leverage a medical system capable of reversible bi-directional adjustment in order to increase the accuracy and/or precision with which the system can be adjusted. For example, during step 904, the actuation section of the shunt will be predictably and reliably moved into a known geometry. This provides a stable and repeatable baseline geometry/size from which any balloon expansion can start from. Given this baseline geometry, the degree of expansion in step 905 can be proportional to other factors in the physician's control (e.g., the volume of expansion media used to expand the balloon during this step). More accurate and precise adjustments of a shunt will allow for improved management of LA and RA pressures, and may lead to improved patient outcomes when treating HF.

Figure 10A:
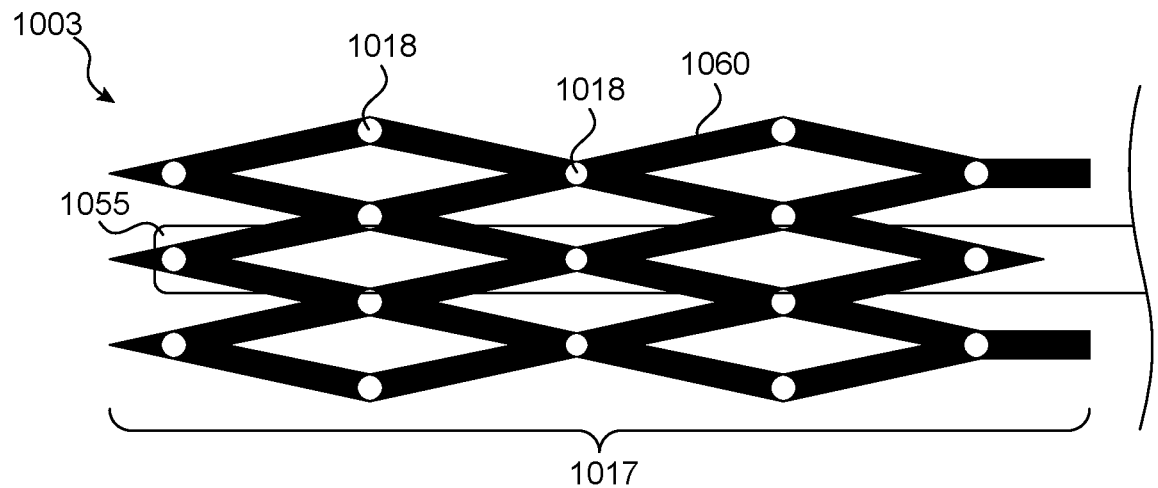
FIGS. 10A and 10B illustrate a distal portion of an energy delivery catheter configured in accordance with embodiments of the present technology.
Figure 10B:
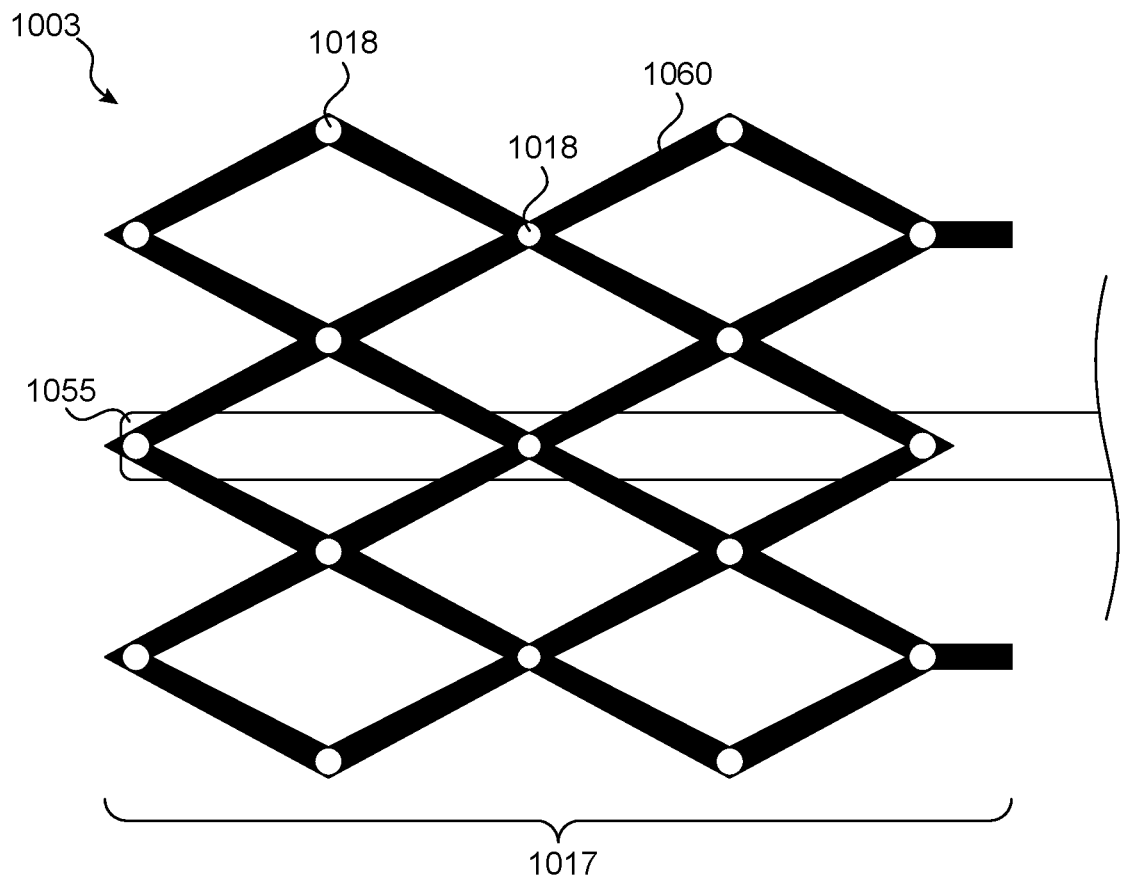

Although the methods 700-900 are described primarily with respect to adjusting a shunt using a balloon, the present technology can also utilize expandable members other than inflatable balloons to adjust the actuation sections of the shunts described herein. For example, FIGS. 10A and 10B show a distal section of an energy delivery catheter 1003 having a distal complex 1017 including an expandable cage or frame 1060 and configured in accordance with embodiments of the present technology. More specifically, FIG. 10A shows a side view of the catheter with the distal complex 1017 in a first, slim-profile configuration, and FIG. 10B shows a side view of the catheter with the distal complex 1017 in a second, relatively expanded configuration. FIGS. 10A and 10B shows example implementations the distal complex 1017 that feature an energy source 1018, which can in some embodiments serve as a combined energy coupling mechanism and actuator expansion component, and other features. For clarity, the proximal portions of catheter 1003 (which can include a handle that is part of a proximal complex (e.g., the proximal complex 422 shown in FIG. 4), power source (e.g., the power source 424 shown in FIG. 4), and other features) are not shown in the figure. However, these components are present within examples of the present technology.

Energy delivery catheter 1003 includes a catheter body or shaft 1055 that connects its proximal portions (e.g., proximal complex) and distal portions (e.g., distal complex 1017). The catheter body 1055 can be substantially similar to the catheter body 655 described above with respect to FIGS. 6A and 6B. The distal complex 1017 can be adapted to interface with the actuation section of an implanted medical device (e.g., cardiac shunt 503). As described above, the distal complex 1017 can include a metallic cage 1060 that may be expanded from a first slimmer configuration (e.g., as shown in FIG. 10A) to a second larger configuration (e.g., as shown in FIG. 10B) by a user, for example by toggling a control feature on a catheter handpiece (not shown) that shortens the length of the cage in a manner that causes it to expand radially. As such, the metallic cage 1060 can apply a radial force to an actuation section of an implanted device and thereby serve as an actuator expansion component (e.g., similar to components 420 and 620).

Energy delivery catheter 1003 can also contain a plurality of electrodes 1018 that can delivery energy (e.g., RF energy) to a component and thereby serve as an energy source (e.g., similar to components 418 and 618). In the implementation shown, energy is produced by a generator located remotely from distal complex 1017 (e.g., in a catheter handle, outside of the catheter, etc.) and transmitted down catheter body 1055 to electrodes 1018. Within examples, electrodes 1018 can directly heat a component in an actuation section of an implanted device. In such examples, the electrodes 1018 would also serve as the energy coupling mechanism (e.g., similar to component 419) in the system. Within alternate examples, electrodes 1018 can be used to heat the metallic cage 1060 or portions thereof, and the metallic cage can transfer heat to a component in an actuation section of an implanted device. In such examples, the metallic cage would also serve as the energy coupling mechanism (e.g., similar to component 419) in the system. In some implementations, some combination of components are used to transfer heat or other forms of energy from the catheter 1003 to a component in an actuation section of an implanted device.

As described above, implementations of the presently disclosed technology involve an expandable compartment (e.g., a balloon) in the distal complex of an energy delivery catheter receiving an energized or energizable medium (e.g., saline). Within examples (e.g., catheter 603) the media can be energized once it has been transferred to the distal complex. This technique may be advantageous to avoid energy loss as the media is transferred through a catheter body to the distal complex. In alternate examples, the media may be energized prior to being transferred to the distal complex (e.g., a medium is pre-heated and injected into the catheter using a syringe that interfaces with a catheter lumen, a medium is injected into the catheter and pre-heated in a compartment that is integral to the catheter but remote from the distal complex prior to being transferred to the distal complex, etc.). Although this technique may result in the media experiencing energy loss prior to it reaching the distal complex, it may lead to more rapid transmission of energy to the actuation complex since the media will arrive at the distal complex energized and not need to undergo an energizing process, which may take time. This could result in faster procedure times, which can benefit physicians, patients and the healthcare system. Some examples of the presently disclosed technologies can utilize multiple energy sources and take a hybrid approach, where media is at least partially energized prior to transfer to the distal complex and then subsequently energized again after transfer to the distal complex. In some instances, this approach could balance the benefit of reducing energy loss experienced by the media as it travels to the distal complex with the benefit of reduced heating time of the media once it is present in the distal complex.

Some implementations of the present technology will include docking or interface features on the implanted device and/or the energy delivery catheter. These features may assist with several aspects of system functionality. In examples, the docking feature(s) facilitate positional stability between a catheter and an implanted device as one or more actions (e.g., an actuation section adjustment) are being performed. This may have particular benefits for devices positioned in certain anatomic locations, for example for cardiac devices where the beating heart can induce unwanted absolute or relative movement of the devices. The docking or interface feature(s) may also facilitate proper alignment of aspects of the system, for example the alignment of an energy source on an energy delivery catheter with a shape memory component in an actuation section of an implanted device. Features that facilitate proper alignment may improve the efficiency of the system, for example by ensuring that any energy/heat generated by the system is delivered exclusively or primarily to the desired regions of the implanted device.

Figure 11A:
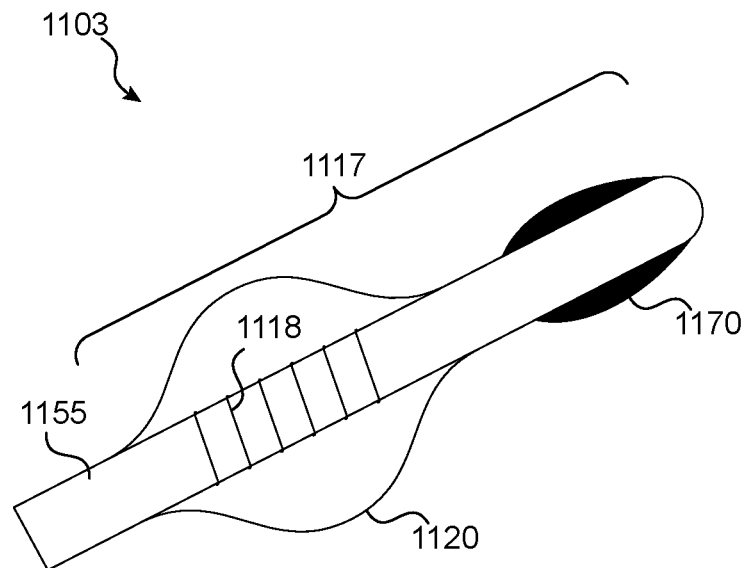
FIGS. 11A-11C illustrate a distal section of an energy delivery catheter including a docking feature and configured in accordance with embodiments of the present technology.
Figure 11B:
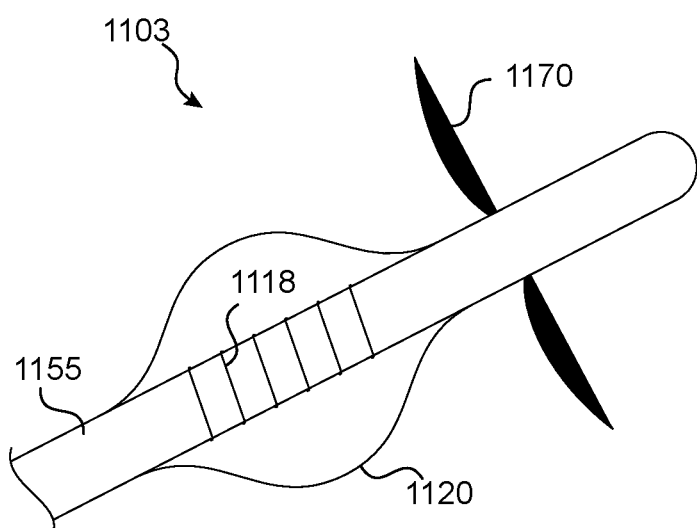
Figure 11C:
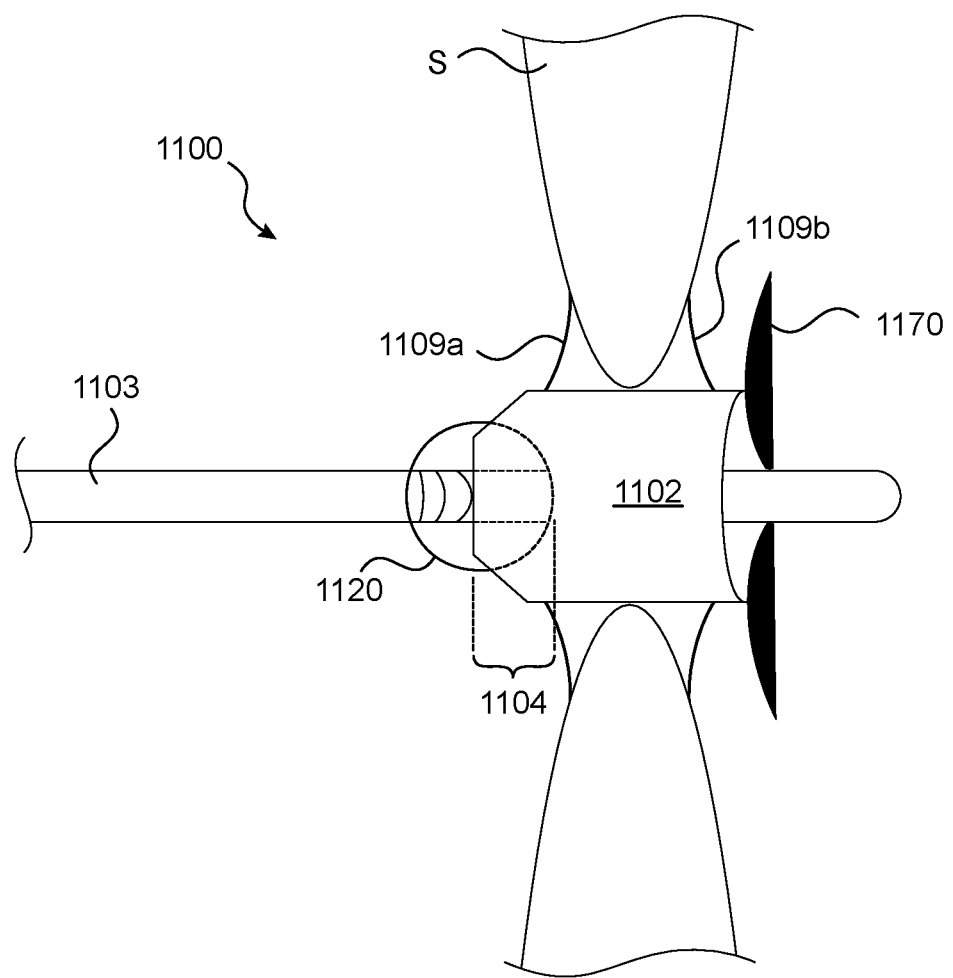

FIGS. 11A-11C, for example, illustrate a distal complex 1117 of an energy delivery catheter 1103 having a docking feature 1170 and configured in accordance with embodiments of the present technology. FIG. 11A shows a side view of the catheter 1103 with the docking feature 1170 in a first configuration. FIG. 11B shows a side view of the catheter 1103 with the docking feature 1170 in a second configuration. FIG. 11C shows a side view of the catheter 1103 as it interfaces with an implanted medical device. The energy delivery catheter 1103 includes a catheter body 1155 and a distal complex 1117. The distal complex 1117 can include an expandable section (e.g., a balloon) 1120 and an energy source (e.g., an electrode) 1118 that can be substantially similar to expandable sections 420 and 620 and energy sources 418 and 618 described above. The distal complex 1117 can also include one or more docking features 1170 located near the distal tip of the catheter. In some implementations, docking features 1170 are established in a fixed position (e.g., a fixed distance away) relative to another feature of the catheter (e.g., the energy source, the actuator expansion component, etc.). Docking features 1170 may be initially in a first, narrow configuration (e.g., as in FIG. 11A) where they are aligned closely to catheter body 1155, giving the catheter a slim profile that can increase maneuverability through small or complex anatomy. When desired, the user can operate a control feature (e.g., a dial that controls one or more pull wires) on a catheter handle (not shown) that deploys the docking features 1170 into a second, expanded configuration (e.g., as in FIG. 11B). As described below, adapting the catheter 1103 into this expanded configuration can increase the stability and positional accuracy of the catheter as it interfaces with an implantable device and facilitate use of the system during a reversible adjustment of the device's geometry.

Referring to FIG. 11C, a system 1100 including the energy delivery catheter 1103 (only distal portion shown for clarity) and an implanted interatrial shunt 1102 is shown according to an example. Shunt 1102 can be substantially similar to implanted devices 102, 402, and 503, and is shown positioned in a septal wall S of a patient. Shunt 1102 can be affixed to the septal wall via a frame and/or via anchors 1109a and 1109b. The RA side of the shunt includes an actuation section 1104 that contains a shape memory component that can be energized and actuated as described above. In an example method of use, a user would first pass catheter 1103 through the lumen of shunt 1102 with the docking features 1170 in a narrow configuration (e.g., similar to as shown in FIG. 11A). With the distal tip of catheter 1103 in the LA, the user can direct the docking features 1170 into an expanded configuration (i.e., as in FIGS. 11B and 11C), and withdraw the catheter position until the docking features 1170 establish contact with the LA side of the shunt frame. Configured in this way, system 1100 can allow for the relative positions of catheter 1103 and shunt 1102 to be fixed, thereby aligning an energy source, energy coupling mechanism, and/or an actuator expansion component with an actuation section of a device.

Within examples of the presently disclosed technologies, implanted devices and/or energy delivery catheters can include thermal insulation components. Thermal insulation components may serve multiple purposes, and in some implementations may serve several purposes simultaneously. In implementations, a thermal insulation component can ensure that energy supplied by an energy delivery catheter to an implanted device does not elevate temperatures in unwanted regions (e.g., in tissue regions, in other regions of the device, etc.). In some implementations thermal insulation components can insulate shape memory components or other actuation components that need to be heated from blood (e.g., blood in an atrium), limiting the thermal quenching effects of the blood volume and thereby allowing more efficient and effective heating of an actuation component. In some implementations, an actuation section may contain multiple shape memory components, and thermal insulation can be used to thermally insulate one component from another to prevent unwanted simultaneous actuation. Thermal insulation can be accomplished using various materials with relatively low thermal conductivity (e.g., ePTFE, silicone, Dacron, polyurethanes, etc.) known to those skilled in the art. For example, an exterior surface of an actuation section membrane (e.g., component 406, shown in FIG. 4) can be comprised of or integrated with a material that limits thermal transfer through the membrane. Such an approach allows for effective thermal transfer to the interior surface of the actuation section (i.e., where an energy delivery catheter would interface) while limiting thermal exposure beyond this region.

Within examples of the disclosed technologies, a geometric dimension of an implanted device can be adjusted bi-directionally, but the total size or footprint of the device (e.g., as defined by the device's outer diameter) remains unchanged during any adjustment. In some implementations, for example, cardiac shunt 503 shown in FIG. 5, the geometries of other portions of the device (e.g., the portion of a shunt lumen defined by a shunt frame 507 and frame membrane 508) in addition to the footprint can also remain stable even when the geometry of a specific portion (e.g., of an actuation section 504) is adjusted. This aspect of the presently disclosed technologies is valuable because it allows an implanted device to be adjusted without risk of accidentally dislodging the device or inadvertently removing the device from the body. In addition, this aspect is valuable because it allows a device geometry to be expanded without stretching or interfacing with soft tissues in any way. Such soft tissue interactions may lead to damage, inflammation, thrombus, pannus formation, and/or other undesirable tissue effects.

As described above, the systems disclosed herein allow for device geometries to adjusted bi-directionally, and adjusted in a manner such that geometry changes are reversible. This aspect of the presently disclosed technologies represents an advancement over the prior art. For example, some existing implanted devices (e.g., stents) can be balloon expanded either during implantation or at a later time due to the malleable nature of the device materials. However, following expansion, these devices cannot be contracted back to the previous geometry. In the context of an interatrial shunt, the capability for reversible and bi-directional adjustment of a shunt lumen offers numerous advantages. For example, if a heart failure patient's condition changes, it may be desired to increase a shunt lumen to allow for a greater volume of fluid flow from the LA to the RA. However, if the patient's condition changes again at a later time, or if the patient's right-heart reacts poorly to the load presented by the additional flow, it may be desirable to undo the shunt lumen increases and revert to a smaller lumen size. Without an ability to accomplish this reversal, many physicians would be hesitant to enlarge a shunt lumen in any patient. Heart failure is a heterogenous and unpredictable disease, and giving physicians an ability to evaluate a particular shunt lumen setting to assess patient response without being permanently locked into the evaluation setting represents a leap forward in the management of these patients.

In some implementations of the presently disclosed technologies, aspects of an implanted device and/or an energy delivery catheter may be designed to be MR-resonant (i.e., excitable via exposure to a magnetic field, for example a magnetic field produced by an MRI machine). In some such implementations, a non-compliant balloon on an energy delivery catheter can have a fixed size, and be placed inside of a lumen/orifice of an implanted device. An actuator element can then be heated using a magnetic field, which could heat the element above a material transition temperature (as described above) and cause the element to contract in size until it is supported by the non-compliant balloon. Such a system can enable precision size adjustments of an implanted device.

As articulated above, there are many suitable implementations of the systems described herein. In some operating conditions, certain implementations may become more practical and/or more favorable for use. For example, with implanted devices in high blood flow regions (e.g., with use of an implanted cardiac device), an energy source comprised of an expelled media (e.g., hot saline or heated foam ejected from the distal complex of an energy delivery catheter) may be cooled by heat sink/quenching effects of the blood volume and also be carried by the blood flow away from the targeted energy delivery region. Accordingly, in operation, it can require additional time, media volume, and/or exposure to impart a phase change in a shape memory component integrally formed with an actuation section of the implant. This can lead to unreliable and/or unacceptable performance of the system. In such high flow operating conditions, the use of directly-applied energy sources (e.g., radiofrequency energy, energy from resistive heating, laser or other optical energy, energy from inductance heating, microwave energy, focused ultrasound energy, etc.) can heat component(s) of an actuation section of an implant more effectively than indirect heating applied via the delivery of an expelled energized media and, therefore, can be less affected by losses related to blood flow. However, use of these energy sources may in some instances be undesirable due to the need for more expensive and sophisticated delivery catheters and more comprehensive safety protocols required to protect tissue structures proximate to the targeted region from experiencing unwanted temperature elevations and/or other undesirable affects during therapy.

In such operating conditions, implementations that utilize a contained, indirectly-applied (i.e., conveyed via an energy coupling mechanism) energy source may be optimal for use. Referring back to FIGS. 6A and 6B, for example, one example of such an implementation is energy delivery catheter 603 comprising an expandable balloon 620 that can be filled with an energized expansion media. Such a configuration is expected to be less resistant to cooling and dissipation effects attributable to blood volume and flow, while maintaining technical simplicity, improved ease-of-use, and relatively improved patient safety.

Figure 12:
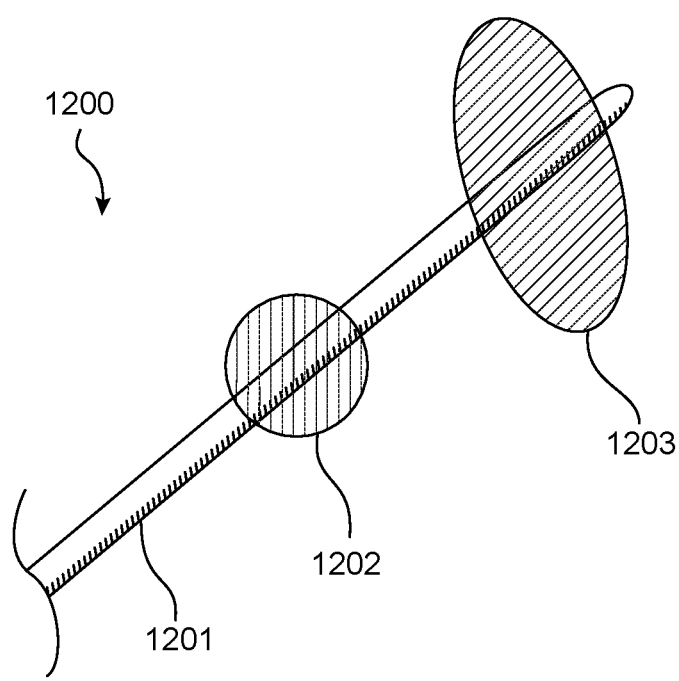
FIG. 12 illustrates a distal end portion of an energy delivery catheter configured in accordance with another embodiment of the present technology.

Further variations of the systems, devices, and methods described herein can be useful to improve the efficiency, accuracy, safety, and/or other attributes of adjustment techniques related to implantable medical devices. FIG. 12, for example, illustrates a distal end portion of an energy delivery catheter 1200 configured in accordance with another embodiment of the present technology. The catheter 1200 may be integrated into part of a medical device system (e.g., system 101, system 401) as described herein. In other embodiments, however, the catheter 1200 may be integrated into other suitable systems.

The catheter 1200 includes a shaft or elongated body 1201 that connects proximal portions of the device (not shown) with the distal complex as illustrated. The catheter 1200 also includes a plurality of expandable balloons, including a first expandable balloon 1202 and a second expandable balloon 1203. In one implementation, the first expandable balloon 1202 may serve as and/or contain an energy source and/or energy coupling mechanism for the catheter 1200. The first and second expandable balloons 1202 and 1203 may be similarly shaped and/or sized, or may have different shapes and sizes. In some embodiments, for example, the second expandable balloon 1203 is larger in at least one dimension and/or has a larger surface area than first expandable balloon 1202. In other embodiments, the second expandable balloon 1203 is smaller in at least one dimension and/or has a smaller surface area than first expandable balloon 1202.

In some embodiments, multiple balloons may be connected to a single lumen to deliver substances (e.g., expansion media) between the proximal portion of the catheter 1200 and the balloons. In still further embodiments, at least one balloon is connected to a lumen that is different than the lumen from at least one other balloon on the catheter 1200.

The first and second balloons 1202 and 1203 can be comprised of similar materials or may be comprised of different materials. In one embodiment, for example, the first balloon 1202 can be a non-compliant or semi-compliant balloon and the second balloon 1203 can be a compliant balloon. In other embodiments, however, the first and/or second balloons 1202 and 1203 may be composed of different materials and/or have different features. It will be understood by one skilled in the art that any number of balloons, with any combination of sizes and materials, with any one or more balloons serving as or and/or containing an energy source and/or energy coupling mechanism, may be utilized within embodiments of the present technology. Further, in some embodiments, one or more alternative expandable features (e.g., an expandable wire cage or mesh, etc.) can be substituted for one or more balloons 1202/1203 of the catheter 1200.

Figure 13A:
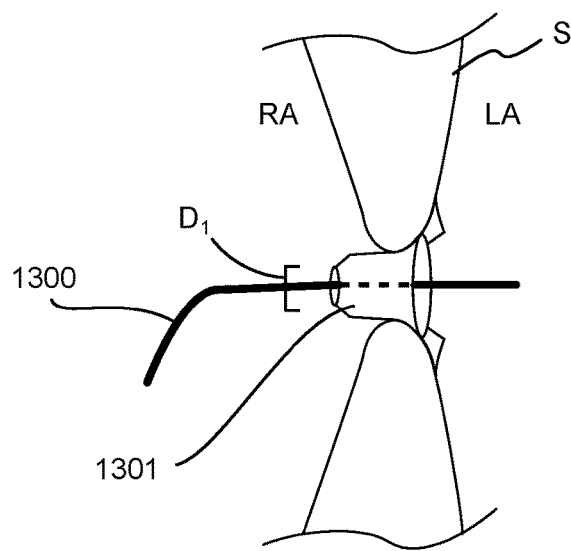
FIGS. 13A-13D are partially schematic, cross-sectional views illustrating representative steps in a method of using the catheter of FIG. 12 to interface with and adjust an implanted medical device in accordance with embodiments of the present technology.
Figure 13B:
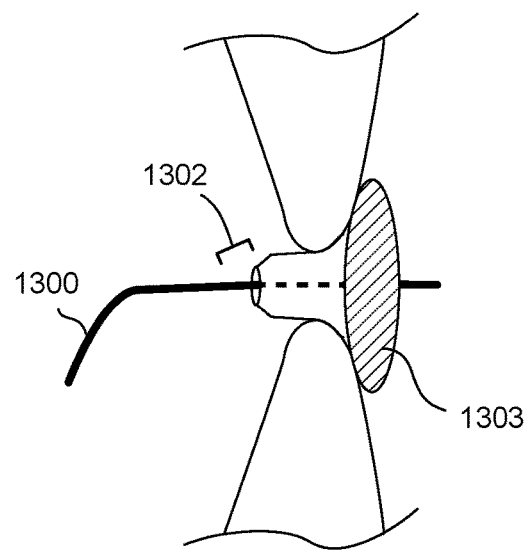

FIGS. 13A-13D are partially schematic, cross-sectional views illustrating representative steps in a method of using the catheter 1200 (FIG. 12) to interface with and adjust an implanted medical device. Referring first to FIGS. 13A and 13B together, an implanted interatrial shunt 1301 has been previously implanted into a sepal wall S of a patient. The shunt 1301 includes at least one actuation section 1302 that resides in the right atrium RA of a patient and that includes a shape memory component (not explicitly shown). For clarity, some features of the shunt device unrelated to the presently described method are not shown and/or are not labeled. In a first configuration (FIGS. 13A and 13B), the actuation section 1302 is configured such that the shunt defines a lumen through which blood may flow between the atria, with the lumen having at least one portion (e.g., an end portion) characterized by a first dimension $D_1$. In an initial step of the disclosed method, the catheter 1200 is positioned inside of the patient's body by a user (e.g., through venous access) and navigated to the RA while the catheter 1200 is in a first, low-profile delivery configuration. As illustrated in FIG. 13A, the catheter 1200 may be passed through the lumen of the shunt 1301 such that a portion of the catheter body extends through the shunt 1301, and portions of the catheter 1200 reside in both the RA and the LA.

With the catheter 1200 positioned as described, a user may expand the second (distal) balloon 1203. In some embodiments, the second balloon 1203 is larger than the shunt lumen and can be larger than the entire shunt structure. In one particular embodiment, after expanding the second balloon 1203, a user may retract the catheter 1200 proximally such that the second balloon 1203 establishes contact with the septal wall and/or the shunt 1301 or structures associated with the shunt 1301. In such a configuration (as best seen in FIG. 13B), the second balloon 1203 can serve as a docking feature (e.g., to help stabilize catheter position), can serve as an alignment feature (e.g., to help align key structures on the catheter with desired corresponding structures on the shunt), as a flow obstruction feature (e.g., to temporarily prevent blood flow through the shunt lumen), and/or for other purposes. It will be further appreciated that retracting the catheter 1200 such that the second balloon 1203 presses against the shunt 1301 and/or the septal wall may help align the location of the catheter 1200 containing the first (proximal) balloon 1202 with an actuation section 1302 of an implanted shunt. Accordingly, retracting the catheter 1200 proximally such that second balloon 1203 presses against the shunt 1301 and/or the septal wall may assist with the dimensional alteration of a shape memory component in an actuation section of the shunt 1301 by occluding the lumen of the shunt 1301 and preventing blood flow therethrough, thereby limiting the heat-sink and/or energy-carrying effects that blood flow traveling through the shunt 1301 may have on energy delivered via the first balloon 1202 (acting as an energy source/energy coupling mechanism) to the shape memory component.

Figure 13C:
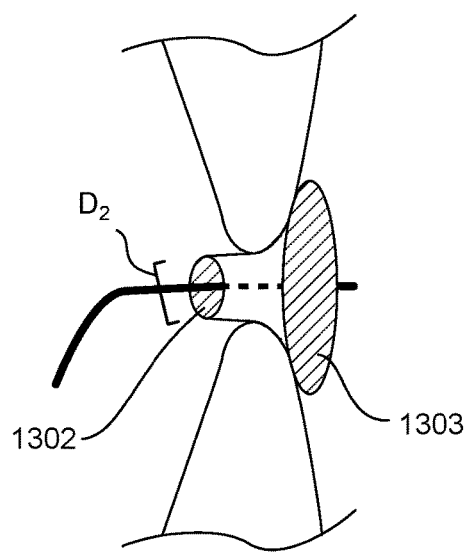

FIG. 13C illustrates an additional step in the method of using catheter 1200 to interface with and adjust the implanted interatrial shunt 1301 (FIG. 13A). In this step, a user expands first balloon 1202 while maintaining the second balloon 1203 in an expanded state and positioned against the LA septal wall and/or shunt. In the illustrate embodiment, the first balloon 1202 aligns with actuation section 1302 (FIG. 13B). In some embodiments, the first balloon 1202 can be filled with an expansion media (e.g., saline, foam, a gas, etc.) having a temperature that is below a phase transition temperature of the shape memory component(s). Given that the shape memory component included in the actuation section 1302 is in a first relatively malleable phase (e.g., a martensitic or R-phase) at temperatures below the phase transition temperature (e.g., at body temperature), inflation of the first balloon 1202 to a size larger than dimension $D_1$ can deform the actuation section 1302 such that an end portion of a lumen expands and can be characterized by a second dimension $D_2$ which is larger than the first dimension $D_1$ (FIG. 13A). In some methods of use, a user can elect to maintain the shunt 1301 with the actuation section 1302 in this expanded configuration characterized by dimension $D_2$ (or more precisely, a dimension similar to $D_2$, since some rebound of the component may occur after an expanding force is removed). In such a method, the first and second balloons 1202 and 1203 may be collapsed by removing the expansion media, and catheter 1200 can disengage from shunt 1301 and be removed.

Figure 13D:
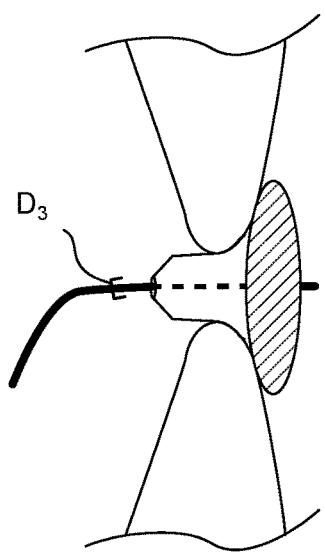

In alternative scenarios, additional and/or alternative dimensional adjustments to the actuation section 1302 may be desired by a user. In such scenarios, additional or alternative method steps may be included. For example, as shown in FIG. 13C, the first balloon 1202 can be expanded to enlarge an actuation section 1302. Alternatively, as best seen in FIG. 13D, the first balloon 1202 can be expanded to a size equal to or smaller than a dimension $D_3$, which could allow balloon surfaces to make contact with or be proximate to actuation section 1302 without mechanically deforming it. Prior to or following delivery of the expansion media to the first balloon 1202, the expansion media may be heated or otherwise energized such that the first balloon 1202 acts directly or indirectly as an energy coupling component that allows a shape memory component in the actuation section to be heated above a phase transformation temperature (e.g., above an R-phase or austenite start or finish temperature) and therefore move towards a manufactured heat-set geometry. Within examples, this geometry may be defined by dimension $D_3$, which is smaller than $D_1$ and $D_2$. In further embodiments, however, $D_3$ may be larger than $D_1$ and $D_2$, or be a dimension sized between or equal to either $D_1$ or $D_2$.

During actuation of the shape memory component, the actuation section 1302 can provide a force that deforms, deflates, or otherwise overcomes the radial outward force provided by the first balloon 1202. For example, as the actuation section 1302 shrinks to a reduced dimension, it may provide a force that pushes expansion media out from the first balloon 1202 and retrograde through a lumen of catheter 1200 towards a proximal end of a device. In some examples, the pressure inside of the first balloon 1202 can be measured using pressure sensors known in the art. As the actuation section 1302 provides a force on the first balloon 1202 during a geometric change to a smaller geometry, there can be an increase in pressure measured inside of the first balloon 1202. This noted increase in pressure may prompt a removal of media from the balloon indirectly (e.g., by alerting a user to perform an action such as withdrawal of media via a syringe) or directly (e.g., by opening a valve in the device to allow for media outflow). In some examples, a valve in the device can be pressure sensitive (e.g., a pressure release, or pop-off, valve) such that as a shape memory component in the actuation section 1302 exerts force on the first balloon 1202. When pressure within the first balloon 1202 increases above a threshold, the valve in fluid (and, therefore, pressure) communication with the balloon media opens and relieves pressure by allowing filling media to flow out of the first balloon 1202. In some embodiments, as a shape memory component of the actuation section 1302 is heated above a transition temperature and begins to move towards a shape set geometry that is smaller than its previous geometry, the expansion media can be slowly removed from the first balloon 1202 to facilitate the actuation section 1302 reaching its preferred geometry without excessive resistance from the first balloon 1202. In some embodiments, this may result in the complete or near-complete removal of expansion media from, and thus the collapse or partial collapse of, the first balloon 1202, as illustrated in FIG. 13D.

Throughout the energy application step(s), the second balloon 1203 may remain expanded and blocking blood flow through the shunt lumen, thereby reducing the cooling and energy distribution effects (e.g., conduction) known to be associated with fluid at one temperature flowing over a surface of a warmer temperature. In the above example, the first balloon 1202 is described to use an expansion media as the energy source and/or energy coupling mechanism, but those skilled in the art will recognize that other energy sources (e.g., radiofrequency (RF) energy, laser energy, ultrasound energy, etc.) and/or coupling mechanisms (e.g., foams, microbubbles, expelled media, direct contact, etc.) can be substituted for the expansion media without loss of novelty.

Figure 14A:
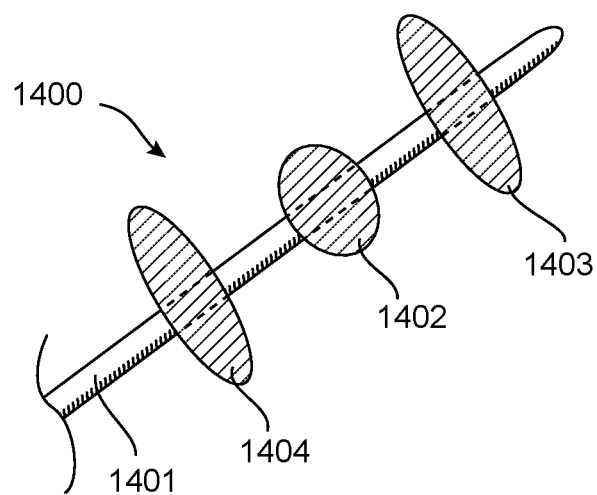
FIG. 14A illustrates a distal end portion of an energy delivery catheter configured in accordance with a further embodiment of the present technology.

FIG. 14A illustrates a distal end portion of an energy delivery catheter 1400 configured in accordance with a further embodiment of the present technology. The catheter 1400 may be similar to catheter 1200 described above and, accordingly, may be integrated into part of a medical device system (e.g., system 101, system 201) as described herein. The catheter 1400 includes a shaft or elongated body 1401 that connects proximal portions of the device (not shown) with the distal complex as illustrated. The catheter 1400 includes three expandable balloons: a first, central expandable balloon 1402, a second, distal expandable balloon 1403, and a third, proximal expandable balloon 1404. The first expandable balloon 1402 serves primarily as an energy source and/or energy coupling mechanism for the catheter 1400 and distal balloon 1403 and proximal balloon 1404 serve primarily as occlusion, docking, and/or positioning mechanisms. In some additional embodiments, the distal and proximal balloons 1403 and 1404 may serve additional purposes related to energy transfer, improving the safety, speed, and/or reliability of the adjustment technique, or other purposes. In the implementation shown in FIG. 14A, the distal and proximal balloons 1403 and 1404 are larger in size than the central balloon 1402. In other embodiments, however, the central, distal, and/or proximal balloons 1402, 1403, 1404 may have different sizes/arrangements relative to each other.

Figure 14B:
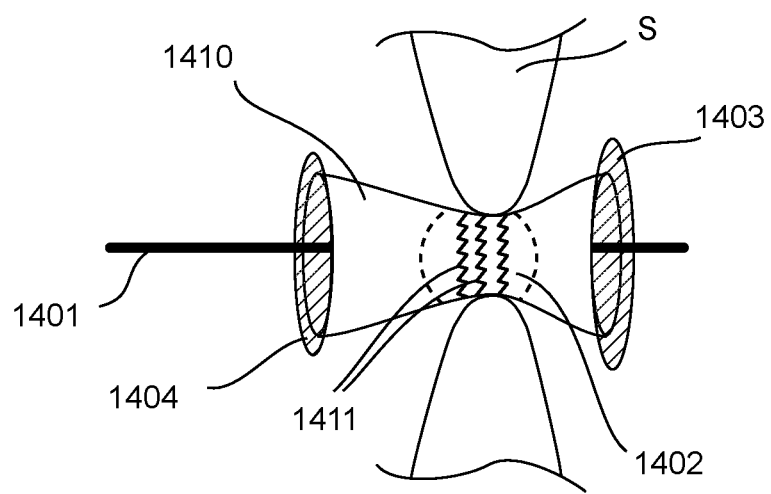
FIG. 14B is a cross-sectional view of the catheter of FIG. 14A interfacing with an interatrial shunt device.

FIG. 14B is a cross-sectional view of the catheter 1400 interfacing with an interatrial shunt device 1410 that has been implanted in the septum S of a patient. The shunt 1410 has a generally parabolic or hourglass shape (as shown), generally cylindrical (not shown), or generally conical (not shown) and includes a central actuation section that contains one or more shape memory components 1411 (e.g., nitinol zig structures, etc.). The shape memory components 1411 may exist in a single portion of the shunt structure, can wrap circumferentially around the shunt structure, or be in another configuration, and can be located inside of, on the exterior of, or embedded within one or more membrane or substrate structures that define a lumen through which fluid may travel, or be positioned in some combination of these locations. In FIG. 14B, the catheter 1400 has been positioned such that it traverses the entire lumen of shunt 1410 and has sections in both the RA and the LA. Both the distal balloon 1403 and proximal balloon 1404 have been expanded to a size larger than the inlet/outlet ends of shunt 1410, and thus block the flow of blood into the central portion of the shunt from either heart chamber, creating an isolation zone interior to the shunt 1410 that limits heat sink/quenching effects both due to the flow of blood through the shunt but also due to the large thermally-conductive volume of blood present in either chamber. Interior to the shunt central balloon 1402 (shown in dashes) can be expanded to alter a dimension of an actuation element as described above.

Figure 15A:
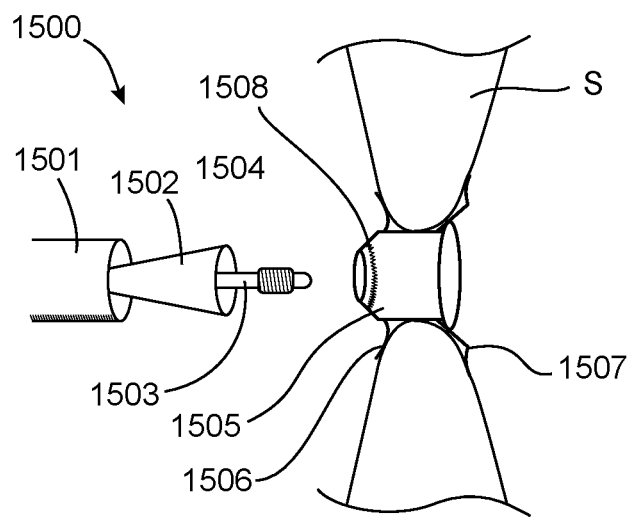
FIGS. 15A and 15B are partially schematic, cross-sectional views illustrating a distal end portion of an energy delivery catheter configured to interface with an interatrial shunt in accordance with another embodiment of the present technology.

FIGS. 15A-15D illustrate additional embodiments of a medical system configured in accordance with the present technology. The figures have been drawn to clearly identify the specific device components associated with the present embodiments, and are not necessarily representative of the relative scale of or spatial relationships between components experienced during use. In addition, some components (e.g., guidewires, frame structures, etc.) have been omitted from the figures for clarity. FIG. 15A, for example, includes a depiction of a catheter device 1500 (only distal end shown) that is configured to interface with an interatrial shunt 1505. The shunt 1505 has been implanted in the septum S of a patient and includes first (e.g., RA side) anchoring elements 1506, second (e.g., LA side) anchoring elements 1507, actuation section 1508, and other features. The catheter device 1500 features a concentric-style design, with outermost portion 1501 comprising a sheath or catheter body that encloses and/or surrounds additional aspects of the device 1500. The innermost portion of catheter device 1500 features an adjustment catheter 1503 that includes one or more expandable balloons 1504. Within implementations, adjustment catheter 1503 can include a number of ports and/or lumens, e.g., lumens intended to convey expansion media to an expandable balloon 1504 or ports that allow the catheter to interface with a guidewire and therefore be delivered over-the-wire as is known in the art.

Figure 15B:
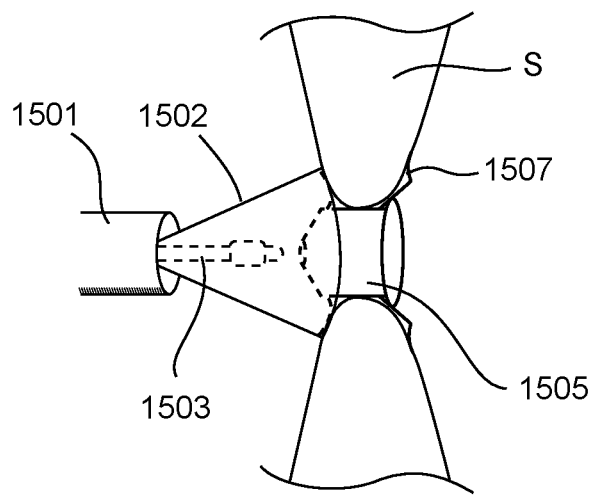

The catheter device 1500 also includes an interface feature 1502 that takes the form of an isolation hood. The isolation hood 1502 can be self-expanding (e.g., constructed at least partially of nitinol or another alloy that has been manufactured to exhibit elastic or superelastic properties at body temperature) and covered with a membrane or substrate that generally has limited to negligible short-term fluid permeability (e.g., a silicone, a urethane, a high density ePTFE, etc.). The isolation hood 1502 can surround the adjustment catheter 1503 and can be advanced to contact and/or surround a portion of the shunt. For example, the isolation hood can be advanced to contact the septal wall surrounding the actuation section 1508 of the shunt (e.g., as shown in FIG. 15B), thereby facilitating the positional stability and alignment of the catheter device 1500 while isolating the actuation section from blood residing in the RA. This isolation (which, in some implementations, can be coupled with additional isolation from blood in the LA) can in some scenarios improve the safety, effectiveness, and reliability of dimensional alterations of a shape memory component located in the actuation section of the shunt as described above, and can in some instances reduce the time required to induce an energy-stimulated geometric change in the actuation section.

Figure 16:
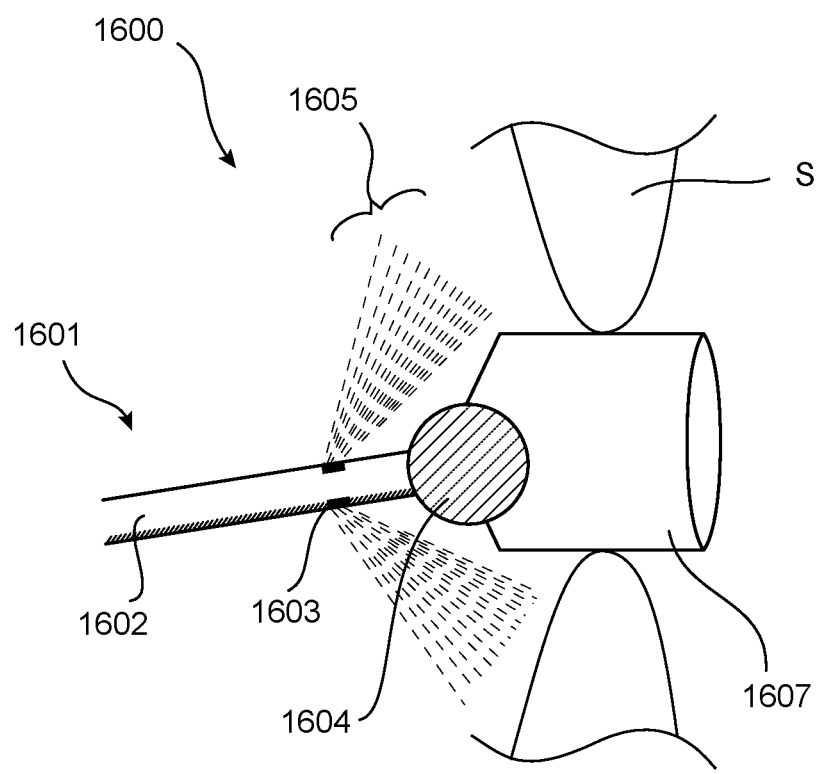
FIG. 16 illustrates a distal end portion of an energy delivery catheter configured in accordance with yet another embodiment of the present technology and interfacing with an interatrial shunt.

Variation implementations of the devices, systems, and methods disclosed herein can optionally incorporate alternative features that assist with bidirectional adjustment of a dimension of an implanted medical device. FIG. 16, for example, illustrates a medical system 1600 comprising an energy delivery catheter 1601 (only distal end shown) interfacing with an interatrial shunt 1607. As shown, the catheter 1601 includes a shaft or elongated body 1602 and a distal complex with an expandable balloon 1604 (shown in an expanded operating configuration) that can act as and/or contain an energy source, actuator expansion component, and/or energy coupling mechanism. The shunt 1607 can be implanted into a septum S and include an actuation section that can be geometrically adjusted in either direction (i.e., either larger or smaller) via the expandable balloon 1604. The catheter 1601 can also feature one or more distal exit ports 1603 through which substances (e.g., saline, contrast agent, pharmaceuticals, foams or gels, etc.) can be expelled from the device. The catheter 1601 can include one or more lumens (not shown) through which substances can travel between the proximal complex of the catheter (e.g., sections proximate to a handpiece outside of a patient's body during use) and the distal portions of the catheter. In some embodiments, a single lumen can transmit substances both to an exit port within an expandable balloon (not shown) and to exit port(s) 1603. In other embodiments, separate lumens can be used to communicate media to the balloon 1604 and to exit ports 1603. In implementations that contain a plurality of exit ports 1603, any combination of shared or independent lumens can be utilized. Identical substances can be passed along multiple lumens or, alternatively, different lumens can serve as pathways for different media. In some examples, identical media may travel along different lumens, but the media traveling through each lumen may be characterized by different properties—for example saline at different temperatures.

During operation of the system 1600, the catheter 1601 can interface with shunt 1607 (as illustrated in FIG. 16). The expandable balloon 1604 can be used to apply a mechanical force to a shape memory component in an actuation section of shunt 1607, resulting in a mechanical deformation of the shape memory component and a corresponding change in the geometry of the shunt 1607 and/or shunt lumen. The expandable balloon 1604 can also apply energy (e.g., in the form of heat) to the shape memory component, resulting in a different geometric change as a consequence of a material phase change due to the shape memory effect, as described elsewhere herein. Prior to, during, or following the application of energy, and regardless of the expanded or deflated condition of the expandable balloon 1604, media 1605 (e.g., saline, a foam, etc.) can be expelled from distal exit ports 1603 in the direction of the expandable balloon 1604, actuation section (not shown), and/or shunt 1607.

The expelled volume of media and/or the associated ejection/streaming force is expected to at least partially prevent blood in the heart chamber from reaching the energy transfer site and acting as a heat sink or as a mechanism to wick away thermal energy via flow. In some embodiments, the expelled media can be a bioabsorbable foam that temporarily occupies the space proximate to the energy transfer site, thereby transiently providing thermal insulation to the site. In alternative embodiments, the expelled media is saline that has been heated to be warmer than body temperature that can displace the blood normally present proximate to the energy transfer site with media that is anticipated to be more insulative to the energy transfer process. In further embodiments, the temperature of the expelled media could be lower than body temperature and be intended to provide cooling to tissue and/or device areas near the energy transfer site (e.g., to provide additional protection against undesirable tissue heating). In some implementations, the balloon 1604 can be perforated such that media (e.g., a hot saline) is also expelled from it during certain operational conditions (e.g., when a threshold pressure inside of the balloon has been reached). It will be appreciated that the most suitable choice of expelled media, along with the temperature and other characteristics of the media, can vary in different operational scenarios and/or when using different implementations of the energy delivery catheters and/or implanted devices described herein.

Figure 17A:
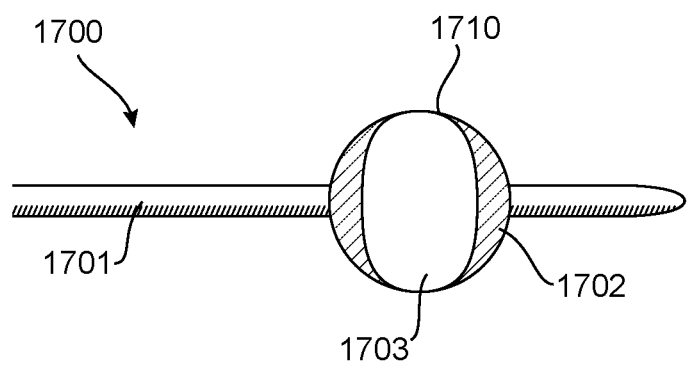
FIGS. 17A-17C illustrate an energy delivery catheter configured in accordance with another embodiment of the present technology.
Figure 17B:
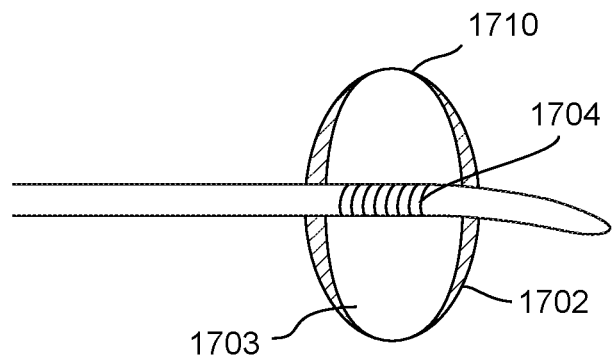
Figure 17C:
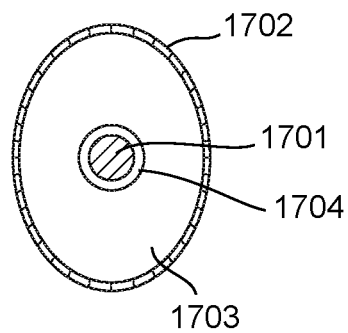

Referring to FIGS. 17A-17E, further embodiments of energy delivery catheters for use with systems and methods described herein are disclosed. FIG. 17A, for example, is a side view of a distal portion of a catheter 1700, while FIG. 17B is a side cross-sectional view of the same catheter 1700. FIG. 17C illustrates a transverse cross-sectional view of the catheter 1700 across a portion of the catheter shaft defined by a region L. As illustrated, the catheter 1700 includes a catheter shaft/elongated body 1701 and a distal complex with an expandable multi-balloon complex or "double-balloon" 1710 (shown in an expanded operating configuration) that can act as and/or contain an energy source, actuator expansion component, and/or energy coupling mechanism. The multi-balloon complex 1710 can include an inner balloon 1703 and an outer balloon 1702. The inner balloon 1703, for example, may be located entirely inside of outer balloon 1702. In other embodiments, however, the outer and inner balloons 1702 and 1703 may have a different arrangement relative to each other.

Both balloons 1702 and 1703 are expandable via the transmission of media via one or more lumens (not shown) that can run between proximal and distal sections of the catheter 1700. In alternate embodiments, only one of the balloons is expanded via a filling media (e.g., a liquid, a gas, a foam, a gel, etc.) and the other balloon may be expanded due to a force (i.e., a pushing or pulling force) provided via a physical attachment to the first balloon. Each balloon 1702 and 1703 may be associated with one or more independent lumens not associated with the other balloon. In other embodiments, however, each balloon 1702 and 1703 may share one or more lumens. Each balloon 1702 and 1703 may be filled or partially filled with the same media (sharing the same characteristics—i.e., temperature—or having varying characteristics) or different media. For example, the inner balloon 1703 can be filled with an energized media to transfer energy to an implanted medical device, and the outer balloon 1702 can be filled with a radiographic contrast agent so as to improve visualization with medical imaging (e.g., with fluoroscopy). Further, it is possible for one balloon to expand while the other balloon remains partially or completely unexpanded. It will be apparent to those skilled in the art that other structures may be substituted for or additionally integrated into one or more of the balloons in the multi-balloon complex. For example, an expandable metallic mesh, cage, or braid can be utilized in conjunction with one or more balloons to achieve similar functionality as described herein.

In some embodiments, the inner balloon 1703 of the catheter 1700 is dimensionally similar to the outer balloon 1702 along at least one dimension. This arrangement is expected to help ensure inner balloon 1703 remains proximate to the intended interface aspects of an implanted device (e.g., proximate to the shape memory component(s) in an actuation section of a device). In the illustrated embodiment, the inner balloon 1703 is approximately cylindrical in shape and, along a region L (FIG. 17B) of catheter shaft 1701, occupies nearly the same spatial area as outer balloon 1702 when both balloons are in an expanded configuration. In other words, when interfaced with a circular or ovular section of an implanted device while in an expanded configuration, inner balloon 1703 will be located proximate to all portions of the section along its rounded perimeter. In other portions of the multi-balloon complex 1710 (i.e., in portions corresponding to locations along the catheter shaft 1701 outside of region L), the balloons may be dimensionally dissimilar.

Referring to FIGS. 17B and 17C, in some embodiments the catheter 1700 can include at least one energy source 1704 within the inner portion of one or both of the balloons 1702 and 1703. The energy source 1704 can be used to directly or indirectly transfer energy (e.g., heat) to an actuation section of an implanted device. The energy source can be, for example, a resistive heating element that can be raised in temperature by running an electrical current therethrough (e.g., via electrical circuitry connected to the energizing element (not shown) that can be included proximate to a handpiece of the catheter). Heat generated by the energy source 1704 can be conveyed via an energy coupling mechanism (e.g., media delivered to and causing the expansion of one or more balloons in the multi-balloon complex 1710 (FIGS. 17A and 17B)) to targeted portions of an implanted device. In some embodiments, saline can be utilized to fill/expand one or more of the balloons such that the multi-balloon complex makes contact with or becomes proximate to an actuation section of an implanted device and also serve as a medium through which heat generated by energy source 1704 is conveyed to the actuation section of the device.

In some embodiments, the energy source 1704 is a metallic wire arranged to have a generally helical shape that wraps around catheter shaft 1701 with at least one turn, and preferably with a plurality of turns. The metallic wire is preferably comprised of a metal with a relatively high electrical resistance, for example nitinol or nickel-chromium. The wire may take on a variety of shapes (e.g., cylindrical, square, flat, etc.) in order to balance ease of manufacturing, structural considerations, and electrical and thermal characteristics. As best seen FIG. 17B, for example, the energy source 1704 comprises a helical metallic wire that has a winding radius larger than that of the catheter shaft it encircles (i.e., the wire encircles the shaft but is offset by some distance and does not contact the shaft along the majority of the length it winds about it). One features of this design is that because it increases the surface area of wire that is in contact with an energy coupling medium, this arrangement is expected to enable more rapid heating of the medium. In other embodiments, the wire may wrap tightly about the catheter shaft. This latter configuration can result in longer heating times, but is expected to enable a slimmer profile energy delivery catheter, which may be a favorable trade-off in certain scenarios.

The use of energy delivering catheters that include multi-balloon complexes (and related implementations) can offer several advantages when integrated into systems and coupled with methods of use as described herein. For example, the use of combinations of different balloon materials (e.g., using coupled compliant and non-compliant balloons) can allow some advantages of the material properties associated with each to be leveraged, which can help with alignment and efficient force transmission when using mechanical means (e.g., via expansion of one or more balloons with filling media) to alter the geometry of an actuation section. Further, when using applied heat to induce a geometry change associated with a shape memory effect, the outer balloon 1702 can serve as a barrier that insulates the heated inner balloon 1703 from blood or other tissues that would otherwise act as heat sinks that pull energy away from the targeted delivery region. In an example implementation, the outer balloon 1702 can be filled with an insulative foam or gel, while an inner balloon can be filled with saline that is to be heated by the energy source 1704. In some embodiments, both inner and outer balloons 1703 and 1702 can be filled with saline and warmed by an energy source (e.g., energy source 1704). In a further embodiment, the outer balloon 1702 can be filled with a cold fluid to spatially contain any temperature rises induced by energized media within inner balloon 1703 to the targeted interface region. An additional advantage of implementations that utilize a multi-balloon complex is that mechanical and thermal energy transfer mechanisms are expected to be jointly improved. For example, outer balloon 1702 with a larger volume and surface area can ensure proper contact, stability, and alignment with an actuation section of an implanted device, and also provide much of the force required to expand the geometry of the actuation section mechanically. Inner balloon 1703 with a smaller volume and surface area will hold a relatively smaller volume of expanding/filling media, which will be energized/heated more rapidly compared to a larger volume of media that could be required when utilizing single balloon approaches.

Figure 17D:
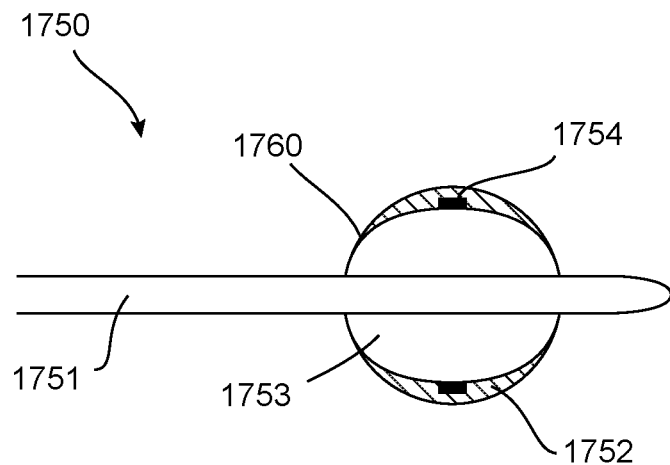
FIGS. 17D and 17E illustrate an energy delivery catheter configured in accordance with a further embodiment of the present technology.
Figure 17E:
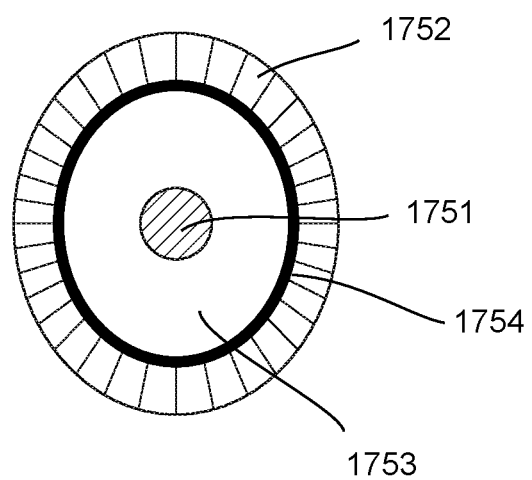

FIG. 17D illustrates a side cross-sectional view of a catheter 1750 configured in accordance with still another embodiment of the present technology, and FIG. 17E illustrates a transverse cross-sectional view of the catheter 1750 of FIG. 17D across a portion of the catheter shaft.

Referring to FIGS. 17D and 17E together, the catheter 1750 is substantially equivalent to catheter 1700 but includes some varied features that may be useful in some scenarios. The catheter 1750 includes a shaft or elongated portion 1751 and features a distal balloon complex 1760 that includes an outer balloon 1752 and an inner balloon 1753. When in an expanded configuration, outer balloon 1752 can assume a roughly spherical shape when not deformed by outside forces. When in an expanded configuration, inner balloon 1753 can be similarly-sized and shaped as outer balloon 1752 along one dimension (e.g., along the dimension parallel to the catheter shaft), but remain smaller than outer balloon 1752 in other dimensions. This dual balloon configuration results in an approximately toroidal shaped space being created between the two balloons when both are expanded. The catheter 1750 further comprises an energy source 1754 that can be coupled to or otherwise closely aligned with the exterior of inner balloon 1753 such that the energy source 1754 is oriented in the open toroidal space. The energy source 1754 can be, for example, an electrode, a resistive wire, a metallic mesh, a laser, an electromagnetic or acoustic energy source, an electromagnetic energy transmission coil, or another suitable energy source known to those skilled in the art. In some embodiments, an electrode or wire-based energy source can be comprised partially or entirely of a superelastic material, and can be machined in to have a zig-zag type pattern when catheter 1750 and distal balloon complex 1760 are in a collapsed or low-profile (i.e., slim) configuration (e.g., for insertion into the body). Such material compositions and component designs, along with similar variants, can allow the energy source 1754 to remain functional as it is expanded between configurations of different geometries.

In one operational example, outer balloon 1752 can be expanded with an electrically and/or thermally conductive medium and thereby either facilitate the conveyance of energy to an actuation section of an implant for direct heating or serve as an energy coupling mechanism to conduct heat indirectly to the actuation section. Such a configuration is expected to have several advantages. For example, the implementation shown in FIGS. 17D and 17E allows for the energy source 1754 comprised of an electrically conductive wire, one or more electrodes, or similar components to be positioned very close to a shape memory component in an implanted device, while keeping the energy source electrically isolated from the patient's body. Further, the toroidal volume in the space between balloons 1752 and 1753 is expected to be much smaller than the volume of either individual balloon 1752 and 1753, which can allow for the balloon(s) to be filled/expanded with a smaller volume of media (enabling the media to be heated with lower overall power delivered), which has the benefit of shorter time requirements to heat the media, smaller energy sources, or both, as described above. Other stated advantages as described above, such as isolating certain portions of the energy delivery catheter from blood flow or from large pools of blood, can also be achieved via catheter 1750 or its variants.

For the presently disclosed devices and systems, the actuation section of an implant can be in a number of potential locations. For example, for an interatrial shunt device, an actuation section can reside in the LA, in the RA, or in a more central portion at or near a septal wall or septal opening. With specific regard to an interatrial shunt device, it may be preferable to have an actuation section that is adjustable in at least one dimension due to the heating of a shape memory component to reside in a location remote from native cardiac tissues (e.g., in an LA or RA). Such a location can reduce the risk of unwanted collateral tissue heating during the transfer of energy from an energy source (e.g., an internal source or an external source) to the shape memory component. Further, the native septal tissue may complicate the functionality of a nearby or integrated actuation section. For instance, the septal tissue can provide resistance to the expansion of a shape memory component during an expansion operation, and following this expansion can provide a radial compressive force that over time could alter the dimension of the actuation section as the septal tissue rebounds/recovers from the expansion operation. Further, during an operation that reduces a dimension of an actuation section that is nearby or integrated into a septal wall, it is possible to create separation between the actuation section or other portions of the device from the septum, which could result in leaks around the device and/or actuation section, or create stagnation zones that elevate thrombus risk. Despite these concerns, some implementations of interatrial shunts and other implantable devices may require and/or benefit from actuation sections that are nearby or integrated into native tissues (e.g., in a relatively central portion of a shunt at or near a septal wall or septal opening). Various device configurations described herein via representative examples are expected to improve the efficacy, safety, and/or practicality of these implementations. It will be clear to those skilled in the art that the configurations as described herein are also expected to be useful, in whole or in part, in implementations of devices that have actuation sections in any location relative to the device or nearby tissues.

Devices configured in accordance with the present technology are also expected to provide combination heating and cooling treatments to tissues and/or structures. In such examples, the application of heating and cooling energy can occur simultaneously or in any sequence relative to one another. Such configurations are expected to be useful in protecting tissues or critical device components from unwanted collateral heating during a time when energy is being transferred to a device to heat a shape memory component in order to induce a material phase change and a corresponding geometric alteration. Some such examples have already been described (e.g., the implementation depicted in FIG. 16). Other such examples can include variations of implementations as previously described herein. For instance, with reference to FIG. 12 and FIGS. 13A-13D, the second balloon 1203 can be filled with a media that is cooler than body temperature. In additional embodiments, the second balloon 1203 can be perforated with openings (for example, openings aimed towards the septal wall S and/or the lumen of shunt 1301—i.e., in the direction of the shape memory component) that can expel a cooled medium (e.g., cold saline) towards the region of targeted energy transfer. In additional embodiments, an energy source or an energy transfer medium contacts a shape memory component directly, effectively transmitting heat and limiting the impact of cooling effects provided by perforated the second balloon 1203. However, other regions (e.g., blood, tissue, other portions of the device) that do not contact the energy source or energy transfer medium directly may receive meaningful cooling effects as a result of a low temperature media being expelled from the second balloon 1203. In some scenarios, this can allow for increased insulation of non-targeted areas from thermal effects while minimizing the impact on procedure time or efficiency related to heating targeted areas. Within examples, various mechanisms can be utilized to directly or indirectly provide a source of cooling thermal energy (e.g., via injection of cold substances, via evaporative cooling, via chemical cooling/endothermic chemical reactions, or via other sources).

Variation examples of energy sources associated with the presently disclosed devices and systems can include thermoelectric (i.e., Peltier) devices. As known to those skilled in the art, thermoelectric cooling devices create cold temperatures in response to electrical currents applied to structures that are constructed to include a junction between two different types of materials. As a consequence of the creation of cold temperatures, a relatively large amount of heat is generally created on the opposing side of the structure. Within an implementation, a thermoelectric device could be utilized to simultaneously provide warming thermal energy to a targeted site (e.g., to a shape memory component) while providing cooling thermal energy to a different region.

In further embodiments, cooling and heating energy may be applied simultaneously to a region, but due to the material properties of a shape memory component relative to those of surrounding structures, temperature elevation (and, thus, a material phase change) can still occur. In one example, a system includes a catheter with an energy source (e.g., one or more radiofrequency energy electrodes) attached to an exterior of an expandable balloon. The balloon can be expanded to make contact with an actuation section of an implanted device and/or surrounding tissues or device structures by filling it with a low temperature media. Through this process, contacted structures are pre-cooled to a temperature lower than body temperature. In one example, radiofrequency energy (provided by another component of the system, for example an RF generator outside of the patient's body) is delivered to the target region via the electrodes affixed to the exterior of the balloon. Without wishing to be bound by theory, due to direct contact/interface and the resistive/thermal properties of a shape memory component relative to surround structures, an applied current may more rapidly induce a temperature elevation in a shape memory component than surrounding tissues or structures. Therefore, a shape memory effect could be induced before temperatures in the surrounding pre-cooled tissues were elevated to undesirable levels.

Figure 18A:
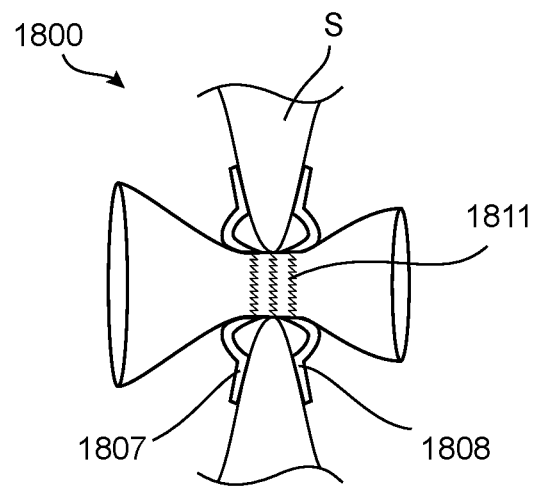
FIGS. 18A-18C illustrate an interatrial shunt assembly configured in accordance with an embodiment of the present technology.
Figure 18B:
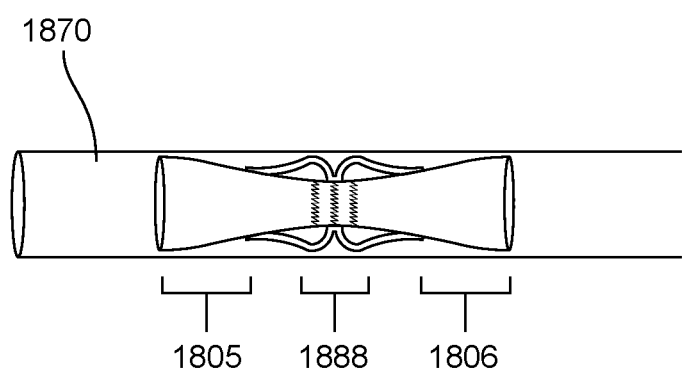
Figure 18C:
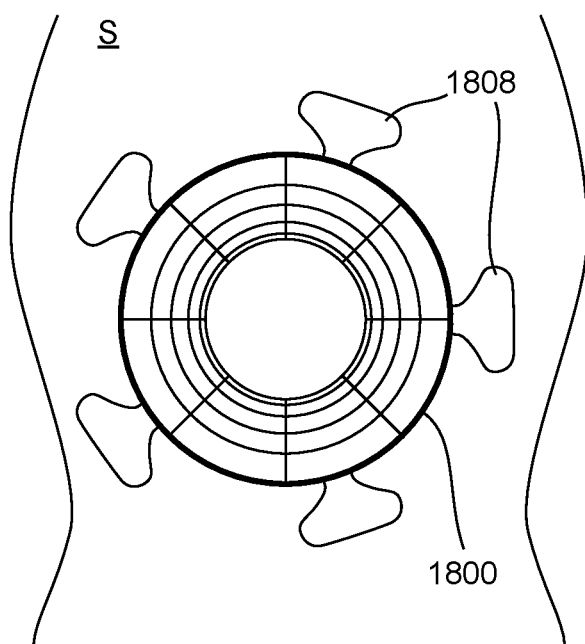

Systems and devices configured in accordance with the present technology are also expected to help improve mechanical, positional, and/or other functional aspects of an implanted device having an actuation section nearby or integrated into a septal wall or another tissue. For example, some implementations of the present technology are expected to help prevent destabilization or leakage associated with an interatrial shunt that has been reduced in a dimension at a location proximate to its contact or securement point with a septal wall. With reference to FIGS. 18A-18C, an example interatrial shunt 1800 includes a first self-expanding end section 1805, a second self-expanding end section 1806, and a centrally-located actuation section 1888 that includes one or more shape memory components 1811 that have been manufactured such that they are relatively malleable at body temperature (i.e., the Af phase transition temperature of the material is above body temperature). In particular, FIG. 18A is partially schematic side view of shunt 1800 implanted into a septal wall S in an expanded operating configuration, FIG. 18B is a side view of the shunt 1800 loaded into delivery catheter 1870 while in a low-profile, collapsed delivery configuration, and FIG. 18C is a transverse view of the shunt 1800 as seen from the LA looking toward the septal wall S after the shunt 1800 is implanted and in its operating configuration.

Referring to FIGS. 18A-18C together, first and second self-expanding sections 1805 and 1806 of the shunt can be comprised of a metallic frame where at least some sections are constructed of superelastic materials (e.g., Nitinol), with the frame being lined with, coated with, encased within, or otherwise integrated with a membrane or substrate material (e.g., a silicone, ePTFE, etc.) that defines a channel through which blood may flow. The first and second self-expanding sections 1805 and 1806 of the shunt can be comprised, for example, of a metallic frame where at least some sections are constructed of conventional linear-elastic-plastic materials (e.g. stainless steel, titanium, cobalt chromium), designed in such a way to achieve shape-memory through elastic recovery (e.g. through a spring-like design), with the frame being integrated with a membrane as described above. The centrally-located actuation section 1888 may be joined or mechanically-coupled to the first and second self-expanding sections 1805 and 1806 such that the three sections form a continuous channel through which fluids may pass. Within examples, the frames of the first and second self-expanding 1805 and 1806 sections and the centrally-located section are composed of a nitinol unibody that spans the entirety of the three sections, with the central frame section being heat-treated and/or otherwise conditioned differently from the end sections during manufacturing such that the material properties of the central frame section differ from those of the frame elements in the first and second self-expanding sections 1805 and 1806. The shape memory components 1811 (in the centrally-located actuation section 1888) can be part of a frame structure, can be separate from a frame structure, can replace a frame structure, or can interface with the other components of shunt 1800 in any other way.

The shunt 1800 also includes first anchoring element(s) 1807 and second anchoring element(s) 1808. In some embodiments, the anchoring elements 1807 and 1808 are also composed of a superelastic material. The first and second anchoring element(s) 1807 and 1808 are shaped/designed so as to grab a variably thick septal wall from opposing sides, and positioned along the body of shunt 1800 such that the first anchoring element(s) 1807 and second anchoring element(s) 1808 exist on opposite sides of the septal wall once shunt 1800 has been deployed into an operating configuration.

As illustrated in FIG. 18B, shunt 1800 can be collapsed (e.g., manually, via an introducer or crimping tool, etc.) into a slim profile delivery configuration and placed within a delivery catheter 1870. When released from the delivery catheter 1870 for implantation into the septum S of a patient (FIG. 18A), the first and second self-expanding sections 1805 and 1806, and first and second anchoring element(s) 1807 and 1808 self-deploy into an operating configuration, while the actuation section 1888 can largely or entirely maintain its slim delivery configuration due to its lack of self-expanding properties at body temperature. In examples where the first self-expanding section 1805 and/or the second self-expanding section 1806 are mechanically-coupled to the central actuation section 1888, a portion of the forces related to the elastic or superelastic recovery of these end sections into their preferred (i.e., heat set, as-manufactured) geometry can be conveyed to the central actuation section and thereby manipulate the central section into a suitable operating configuration. In other implementations of systems and methods, the central actuation section 1888 may be required to be forced open (e.g., by an initial balloon expansion that is an integral step in a device delivery procedure) to achieve its desired operating configuration. In variation embodiments, the as-delivered geometry of the central actuation section is suitable for use.

As illustrated in FIG. 18A, in an operating configuration shunt 1800 assumes an hourglass type shape, with relatively wide flared end sections that serve as inlets/outlets for blood flow that taper down to a centrally-located smaller neck region that interfaces with the septal wall. Radial outward force provided by the central section 1888 help stabilize the position of shunt 1800. The flared geometry of end sections 1805 and 1806 further anchor the shunt in place, as the size of the shunt body exceeds the size of the transseptal opening that is created during device delivery. In a non-adjustable configuration, the geometry of the frame section of shunt 1800 can be sufficient to ensure proper shunt functionality and prevent migration. However, with an adjustable shunt—particularly with an adjustable shunt that can be made smaller in a geometric dimension—additional anchoring elements 1807 and 1808 can improve the function and stability of the device.

The first and second anchoring element(s) 1807 and 1808 can be attached to or otherwise integrated with the shunt body (e.g., via welding, sutures, adhesives, shared membrane integration, etc.) and configured to have at least some sections that will lie approximately flush with the sides of the septal wall when the shunt 1800 is in an operating configuration, as shown in FIG VA and VC. In variations that included materials and/or surface treatments to allow/promote tissue-growth, once implanted in this configuration, after a period of time (e.g., 6-12 months) it is expected that the first and second anchoring elements 1807 and 1808 will experience tissue overgrowth and/or endothelialization, and therefore become embedded in the septal wall. This design is expected to be advantageous as, over time, it allows for more effective structural integration of the shunt 1800 into the septal wall. Accordingly, if at a time several months after implantation (e.g., once anchoring elements have grown into the septal wall) a user wished to alter the geometry of the shunt in a way that reduced a dimension at or near the central actuation section 1888, the adjustment procedure is less likely to create gaps between the septal wall and the shunt, thereby preventing leaks around the shunt or stasis areas of low blood flow that can lead to thrombus or emboli. More specifically, in many cases it is expected that a shunt device would be placed into the septal wall in the region of the fossa ovalis, and anchoring elements 1807-1808 would interface at least in part with thin and relatively stretchable primum tissue. Accordingly, the force generated by shape memory components 1811 in the actuation section 1888 of shunt 1800 as they change material phase and move towards a preferred heat-set geometry can, in many instances, overcome any counterforce enacted by the primum, thereby stretching the primum towards the shunt body as it moves. Within example clinical scenarios, this can facilitate the maintenance of a tight seal between the shunt device and the surrounding tissue, which is expected to further improve performance and increase the safety profile of the device.

A number of implementations of energy delivery catheters described herein include expandable balloons that can be used to apply mechanical force to an actuation section of an implantable device to cause it to deform geometrically (e.g., expand or contract in a dimension) and/or be used to provide or convey heat to a shape memory component within an actuation section to cause a change in geometry related to a material phase change. In some scenarios, preferable implementations can utilize a compliant balloon (i.e., constructed from silicone, a polyurethane, or similar materials) that, after expansion and subsequent collapse, returns to a thin profile that is positioned tight and close to the body of a catheter shaft. Such a configuration may allow for smaller diameter delivery tools (e.g., catheters, sheaths, introducers, etc.) relative to the use of a non-compliant balloon, which in general will not automatically regain a thin profile once it has been expanded out of an initially folded configuration.

A challenge with using compliant balloons to interface with implanted medical devices, particularly devices that have an actuation section with a small length along the axis of a catheter shaft, is that alignment between the balloon and the targeted interface area can be difficult. Further, as a compliant balloon expands to engage such a structure smaller in length the balloon, it can tend to "buckle" outward around the end edges of a structure instead of expanding outward radially so as to apply sufficient concentrated force to the structure to cause a mechanical deformation. Utilization of specific geometry balloons can facilitate overcoming such challenges. For example, a balloon that is large radially in dimensions outward from the catheter body compared to its length along the catheter body can be preferable for use. Such a balloon geometry is inherently constrained to a fixed length along the dimension of the catheter shaft, which is expected to help prevent excess end-buckling as it expands to engage a similar length structure. In one example, an energy delivery catheter includes a compliant balloon with approximate dimensions of 10 mm diameter×40 mm long such that, in an expanded configuration, the balloon is roughly shaped as a cylinder. In some embodiments, the wall thickness of one or more balloons utilized in a catheter as described herein may vary across different aspects of the balloon, thereby altering the expansion and mechanical properties of the balloon in a way to better enable functionality with engaging and deforming an implantable device. In several embodiments, balloons can be injection molded to allow for strong manufacturing yield and precision while creating a balloon with variable wall thickness.

An energy delivery catheter configured in accordance with the present technology can utilize a tapered actuator expansion component (e.g., a tapered balloon, a tapered metallic mesh, etc.). The tapered component can move between a relatively flat and uniform delivery configuration (e.g., one in which it resides entirely in close proximity with a catheter shaft or body), and an expanded operating configuration where it has a tapered shape that in a first location extends a first distance from the catheter shaft and in a second location extends a second distance from the catheter shaft. In some examples, the tapered component can include one or more marker bands (e.g., radiopaque markers, echogenic markers, etc.) positioned at points along the taper. For example, marker bands placed at locations where the taper extends 1 mm, 2 mm, 3 mm, etc. away from the catheter shaft. Any number of marker bands at any number of intervals can be utilized.

During a procedure involving the mechanical expansion of an actuation section of an implanted device, a catheter could first interface with the device while in its slimmer low-profile delivery configuration. For instance, a user could place the distal end of the catheter through the lumen of an interatrial shunt. The tapered expansion component could then be expanded entirely or partially into an operating configuration. In some examples, the taper direction is such that the expansion component becomes larger (i.e., expands more radially from a catheter shaft) as it becomes further away from the actuation section of the device when positioned as currently described. To enlarge the actuation section, a user could begin to retract the catheter such that the tapered section interfaces with a relatively malleable component and forces it to expand. The degree of expansion is directly related to the size of the tapered expansion component at the interface point with the actuation section, which is controlled by the degree to which a user retracts the catheter with the expansion component expanded into an operating configuration. Medical imaging (e.g., fluoroscopy, ultrasound, etc.) can help guide the user by showing positions of marker bands on the tapered component relative to the position of the actuation section (which can be generally visible, all or in part, with imaging). Once a user has retracted the catheter sufficiently so as to position the tapered expansion component properly in order to create the desired amount of dilation of the actuation section, the user can move the tapered component back into its slimmer delivery configuration for removal. As one skilled in the art will recognize, the above procedure steps are intended to be illustrative in nature and are not exhaustive, and other steps that are complimentary, substitutive, or additive to the above procedure as described can be included.

The devices and systems described herein can feature catheters with one or more lumens. Lumens can serve as passageways for components of a delivery or adjustment system (e.g., for a guidewire), be used to transport media between proximal and distal ends of the catheter, and/or for other purposes. In some implementations, a lumen in a catheter can be unidirectional in nature—in other words, it serves as a conduit intended to pass media that moves strictly in one manner relative to the catheter (e.g., from a proximal end towards a distal end, from a distal end towards a proximal end, etc.). In such implementations, catheters can have a plurality of lumens, e.g., lumens to provide expansion media to expandable balloons and lumens to remove media from expandable balloons. In other implementations, lumens can be bidirectional and capable of moving media back and forth within the catheter. For example, a syringe can interface with an entry port near a proximal end of the catheter, and media can be delivered or removed from the distal ends of the catheter depending on whether a user is depressing or withdrawing the syringe plunger. In another example, media can be provided into a catheter via a first means (e.g., a syringe, an IV bag, etc.) and be removed via a different means (e.g., via a one-way valve that diverts retrograde flow of media towards an exit port).

A number of the devices, systems, and methods described herein involve changing a temperature in a portion of a catheter, implanted device, or in another region. In some implementations, it is desirable to measure, display/communicate, or control temperature changes induced in a portion of the system. In some examples, direct or indirect feedback loops can be utilized to control temperatures in regions of the system, which facilitates both ensuring the temperatures meet their targeted levels as well as ensuring temperatures remain within safe operating limits. In an example, a temperature sensor (e.g., a thermocouple, a thermistor circuit, etc.) can be included at or near a portion of the system where a temperature change is induced. Measured temperatures can be displayed to a user (e.g., on a display proximate to the handpiece or elsewhere outside of the patient's body), or indicators depicting the general state of the temperature (e.g. green indicator for favorable temperature, red indicator for undesirable temperature, etc.) can be provided. In some examples, circuitry such as an NTC thermostat can be used to regulate temperature in a temperature-controlled element.

B. Interatrial Shunts for Treatment of Heart Failure

In some embodiments, the systems and methods described herein are used for treating heart failure. Heart failure can be classified into one of at least two categories based upon the ejection fraction a patient experiences: (1) heart failure with reduced ejection fraction (HFpEF), historically referred to as diastolic heart failure or (2) heart failure with preserved ejection fraction (HFrEF), historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Figure 19:
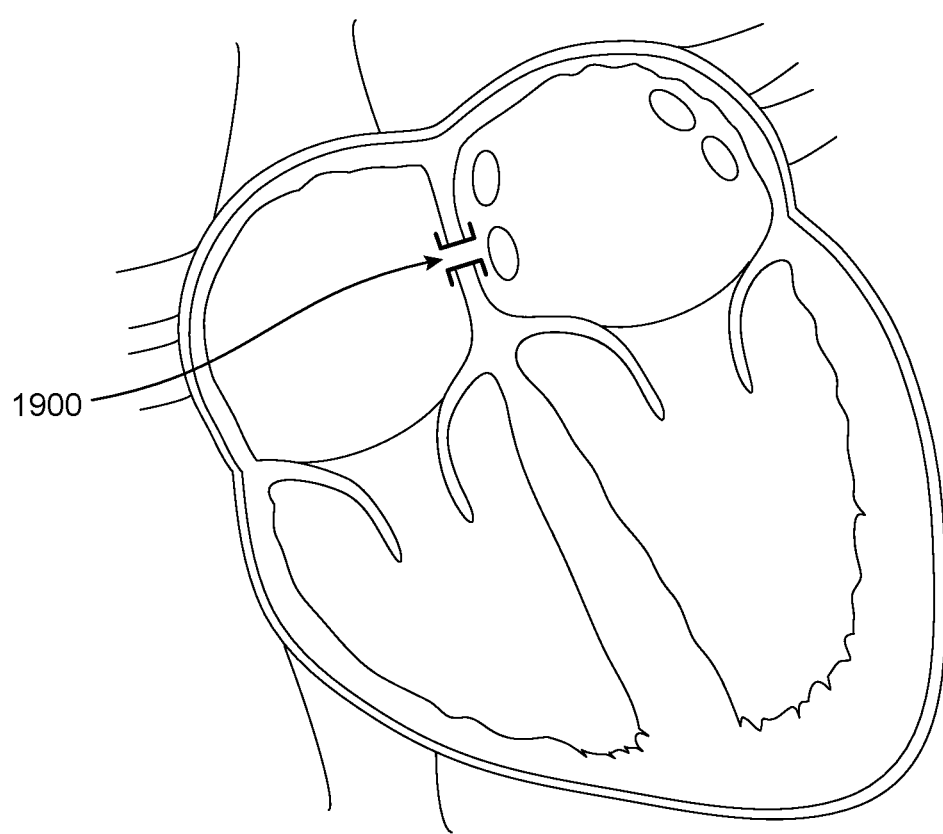
FIG. 19 is a schematic illustration of an interatrial device implanted in a heart and configured in accordance with an embodiment of the present technology.

Interatrial shunts have recently been proposed as a way to reduce elevated left atrial pressure, and this emerging class of cardiovascular therapeutic interventions has been demonstrated to have significant clinical promise. FIG. 19 shows the conventional placement of a shunt in the septal wall between the LA and RA. Most conventional interatrial shunts (e.g., shunt 1900) involve creating a hole or inserting a structure with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With many such traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select shunt size—perioperatively or post-implant—based on the patient and, as discussed above with respect to FIGS. 1-6B, allow for non-invasive monitoring of lumen geometry to determine whether lumen adjustments would be beneficial and/or confirm whether lumen adjustments were successful.

As one of skill in the art will appreciate from the disclosure herein, various features of the methods and systems described above can be omitted without deviating from the scope of the present technology. Likewise, additional features not explicitly described above may be added to the methods and systems without deviating from the scope of the present technology. Accordingly, the methods and systems described herein are not limited to those configurations expressly identified, but rather encompasses variations and alterations of the described methods and systems. Moreover, the following paragraphs provide additional description of various aspects of the present technology. One skilled in the art will appreciate that the following aspects can be incorporated into any of the methods and systems described above.

Conclusion

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols and at other frequencies, as is known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

Embodiments of the present disclosure may be implemented as computer-executable instructions, such as routines executed by a general-purpose computer, a personal computer, a server, embedded computer, or other computing system. The present technology can also be embodied in a special purpose computer or data processor that is specifically programmed, configured, or constructed to perform one or more of the computer-executable instructions explained in detail herein. The terms "computer" and "computing device," as used generally herein, refer to devices that have a processor and non-transitory memory, as well as any data processor or any device capable of communicating with a network. Data processors include programmable general-purpose or special-purpose microprocessors, programmable controllers, ASICs, programming logic devices (PLDs), or the like, or a combination of such devices. Computer-executable instructions may be stored in memory, such as RAM, ROM, flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the LA and RA, the LV and the right ventricle (RV), or the LA and the coronary sinus, it should be appreciated that similar embodiments could be utilized for shunts between other chambers of heart or for shunts in other regions of the body. Furthermore, while various embodiments of the technology described herein are directed to implantable shunts, it will be appreciated that the technology described in the present disclosure may also be utilized with a variety of different implantable medical devices in addition to shunts.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of adjusting a dimension of a shunt fluidly coupling a first body region and a second body region, the method comprising:
   advancing an elongated body through the patient's vasculature and toward the implanted shunt, wherein the elongated body includes an expandable member;
   positioning the elongated body within a flowpath extending through the shunt or proximate to the opening of the shunt orifice; and
   heating, via the elongated body, a shape memory component of the shunt, wherein heating the shape memory component transforms the shunt from a first configuration to and/or toward a second configuration,
   wherein transforming the shunt from the first configuration to and/or toward the second configuration reduces an inner dimension of the shunt associated with the flowpath without substantially altering an outer dimension of the shunt such that the shunt remains anchored to patient tissue proximate the first body region and the second body region.

2. The method of claim 1 wherein heating the shape memory component comprises heating via the expanded expandable member.

3. The method of claim 1 wherein, after heating the shape memory component and decreasing the inner dimension associated with the flowpath, selectively expanding the expandable member to selectively increase the inner dimension associated with the flowpath.

4. The method of claim 3 wherein decreasing the inner dimension associated with the flowpath decreases a flow of fluid through the flowpath, and wherein increasing the inner dimension associated with the flowpath increases the flow of fluid through the flowpath.

5. The method of claim 1 wherein the shunt is configured to retain the reduced dimension until the expandable member is expanded.

6. The method of claim 1 wherein the inner dimension is a diameter of the flowpath and/or flowpath orifice.

7. The method of claim 1 wherein the outer dimension is a diameter of a frame of the shunt.

8. The method of claim 1 wherein heating the shape memory component includes heating the shape memory component above a transition temperature to transition the shape memory component from a first material phase to a second material phase, and wherein the transition temperature is a temperature greater than body temperature.

9. The method of claim 1 wherein the elongated body includes a catheter.

10. A method of adjusting a dimension of a shunt anchored between and fluidly coupling a first body region and a second body region of a patient, the method comprising:
    advancing an elongated body through the patient's vasculature and toward the implanted shunt;
    positioning the elongated body within a flowpath extending through the shunt and/or proximate to an opening of the shunt orifice; and
    heating, via the elongated body, a shape memory component of the shunt, wherein heating the shape memory component transforms the shunt from a first configuration to and/or toward a second configuration,
    wherein transforming the shunt from the first configuration to and/or toward the second configuration reduces an inner dimension of the shunt associated with the flowpath and/or the shunt orifice while maintaining an outer dimension of the shunt such that the shunt remains anchored between the first body region and the second body region.

11. The method of claim 10 wherein the elongated body includes a catheter.

12. The method of claim 11 wherein the catheter includes a radiofrequency and/or an electromagnetic source, and wherein heating the shape memory component includes using the radiofrequency source and/or the electromagnetic source to heat the shape memory component.

13. The method of claim 10, further comprising, after transforming the shunt from the first configuration to the second configuration:
    transforming the shunt from the second configuration to and/or toward a third configuration, wherein transforming the shunt to and/or toward the third configuration increases an inner dimension of the shunt associated with the flowpath and/or orifice while maintaining the outer dimension of the shunt.

14. The method of claim 13 wherein transforming the shunt from the second configuration to and/or toward the third configuration includes mechanically expanding the shunt.

15. The method of claim 10 wherein heating the shape memory component includes heating the shape memory component above a transition temperature to transition the shape memory component from a first material phase to a second material phase, and wherein the transition temperature is a temperature greater than body temperature.

16. A method of adjusting a dimension of an interatrial shunt anchored to a septal wall of a patient and fluidly connecting a left atrium and a right atrium of a patient's heart, the method comprising:
    advancing an elongated body through the patient's vasculature and toward the implanted shunt;
    positioning the elongated body within a flowpath extending through the shunt and/or proximate to an opening of the shunt orifice; and
    heating, via the elongated body, a shape memory component of the shunt, wherein heating the shape memory component transforms the shunt from a first configuration to and/or toward a second configuration,
    wherein transforming the shunt from the first configuration to and/or toward the second configuration reduces an inner dimension of the shunt associated with the flowpath and/or the shunt orifice while the shunt remains anchored to the septal wall.

17. The method of claim 16 wherein reducing the inner dimension of the shunt reduces a flow of blood through the shunt.

18. The method of claim 16 further comprising, after transforming the shunt from the first configuration to the second configuration, mechanically expanding the shunt from the second configuration to and/or toward a third configuration to increase the inner dimension.

19. The method of claim 16 wherein heating the shape memory component includes heating the shape memory component above a transition temperature to transition the shape memory component from a first material phase to a second material phase.

* * * * *